United States Patent
Kung et al.

(10) Patent No.: US 7,678,819 B2
(45) Date of Patent: Mar. 16, 2010

(54) ACETYLENE DERIVATIVES AND THEIR USE FOR BINDING AND IMAGING AMYLOID PLAQUES

(75) Inventors: Hank F. Kung, Wynnewood, PA (US); Mei Ping Kung, Wynnewood, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 11/951,612

(22) Filed: Dec. 6, 2007

(65) Prior Publication Data
US 2008/0166299 A1  Jul. 10, 2008

Related U.S. Application Data

(60) Provisional application No. 60/873,249, filed on Dec. 7, 2006.

(51) Int. Cl.
A61K 31/44 (2006.01)
C07D 213/24 (2006.01)
C07D 213/56 (2006.01)

(52) U.S. Cl. .................. 514/357; 546/334; 564/336
(58) Field of Classification Search ............... 564/161, 564/336; 546/337, 334; 514/357
See application file for complete search history.

(56) References Cited

U.S. PATENT DOCUMENTS

2004/0023479 A1  2/2004  Tour et al.

2007/0242322 A1  10/2007  Fukuda et al.

FOREIGN PATENT DOCUMENTS

| JP | 2001-089407 A | 4/2001 |
| WO | WO 02/13764 A2 | 2/2002 |
| WO | WO 2005/094822 A1 | 10/2005 |
| WO | WO 2006/115895 A2 | 11/2006 |

OTHER PUBLICATIONS

Hcaplus 130:124870.*
Patent Abstracts of Japan, Publication No. 2001089407, published Apr. 3, 2001, Fuji Photo Film Co. Ltd.
Agdeppa, E.D. et al., "Binding Characteristics of Radiofluorinated 6-Dialkylamino-2-Naphthylethylidene Derivatives as Positron Emission Tomography Imaging Probes for $^\beta$-Amyloid Plaques in Alzheimer's Disease," J. Neurosci., 2001, 21 RC189, 1-5.
Agdeppa, E.D. et al., "In vitro detection of (S)-naproxen and ibuprofen binding to plaques in the Alzheimer's brain using the positron emission tomography molecular imaging probe 2-(1-[6-[(2-[(18)F]fluoroethyl)(methyl)amino]-2-naphthyl]ethylidene)malononitrile," Neuroscience. 2003;117:723-30.

(Continued)

*Primary Examiner*—Janet L Andres
*Assistant Examiner*—Binta M Robinson
(74) *Attorney, Agent, or Firm*—Woodcock Washburn LLP

(57) ABSTRACT

The invention relates to radiolabeled compounds and their use in methods of imaging amyloid deposits, as well as to methods of their manufacture. The invention also relates to compounds for inhibiting the aggregation of amyloid proteins that form amyloid deposits, methods for delivering therapeutic agents to amyloid deposits, as well as methods of making compounds that inhibit the aggregation of amyloid proteins.

24 Claims, 11 Drawing Sheets

OTHER PUBLICATIONS

Armstrong, R.A., "Plaques and tangles and the pathogenesis of Alzheimer's disease," Folia Neuropathol 44:1 (2006).

Ashburn, T.T. et al., "Amyloid probes based on Congo Red distinguish between fibrils comprising different peptides," Chem. Biol, 3:351-358 (1996).

Bacskai, B.J. et al., "Four-dimensional multiphoton imaging of brain entry, amyloid binding, and clearance of an amyloid-beta ligand in transgenic mice," Proc Natl Acad Sci U S A, 100:12462 (2003).

Bacskai, B.J. et al., "Imaging of amyloid-beta deposits in brains of living mice permits direct observation of clearance of plaques with immunotherapy," Nat Med 7:369, (2001).

Barrio, J.R. et al., "PET imaging of tangles and plaques in Alzheimer's disease with a highly hydrophobic probe," J Lab Compds Radiopharm, 1999, 42 Suppl. 1:S194-S195.

Barrio, J.R. et al., "PET imaging of tangles and plaques in Alzheimer's disease," J Nucl Med 40:70P, (1999b).

Berezovska, O. et al., "Familial Alzheimer's disease presenilin 1 mutations cause alterations in the conformation of presenilin and interactions with amyloid precursor protein," J Neurosci 25:3009 (2005).

Berge S.M. et al., "Pharmaceutical Salts," J. Pharm. Sci. 66:1 19 (1977).

Blennow, K. et al "Pinpointing plaques with PIB," Nat Med 12:753-754 (Jul. 2006).

Boss, M.A., "Diagnostic approaches to Alzheimer's disease," Biochim Biophys Acta 1502:188 (2000).

Buckner, R.L. et al., "Molecular, structural, and functional characterization of Alzheimer's disease: evidence for a relationship between default activity, amyloid, and memory" J Neurosci 25:7709 (2005).

Catalano, S.M. et al., "The Role of Amyloid-Beta Derived Diffusible Ligands (ADDLs) in Alzheimer's Disease" Curr Top Med Chem 6:597 (2006).

Deng, Y. et al., "Deletion of presenilin 1 hydrophilic loop sequence leads to impaired gamma-secretase activity and exacerbated amyloid pathology" J Neurosci 26:3845 (2006).

Dezutter, N.A. et al., "99mTc-MAMA-chrysamine G, a probe for beta-amyloid protein of Alzheimer's disease," Eur J Nucl Med 26:1392 (1999).

Elhaddaoui, A. et al., "Competition of congo red and thioflavin S binding to amyloid sites in Alzheimer's diseased tissue," Biospectroscopy 1:351 (1995).

Engler, H. et al., "Two-year follow-up of amyloid deposition in patients with Alzheimer's disease," Brain (2006).

Findeis, M.A., "Approaches to discovery and characterization of inhibitors of amyloid β-peptide polymerization," Biochimica et Biophysica Acta 1502:76-84, 2000.

Frey, K.A., "Neurochemical imaging of Alzheimer's disease and other degenerative Dementias," Q J Nucl Med 42:166 (1998).

Fryer, J.D. et al., "Apolipoprotein E markedly facilitates age-dependent cerebral amyloid angiopathy and spontaneous hemorrhage in amyloid precursor protein transgenic mice," J Neurosci 23:7889 (2003).

Ginsberg, S.D. et al., "Molecular Pathology of Alzheimer's Disease and Related Disorders," in Cerebral Cortex: Neurodegenerative and Age-related Changes in Structure and Function of Cerebral Cortex, Kluwer Academic/Plenum, NY (1999), pp. 603-654.

Golde, T.E. et al., "Biochemical detection of Aβ isoforms: implications for pathogenesis, diagnosis, and treatment of Alzheimer's disease," Biochimica et Biophysica Acta 1502:172-187 (2000).

Golde, T.E., "The Abeta hypothesis: leading us to rationally-designed therapeutic strategies for the treatment or prevention of Alzheimer disease," Brain Pathol 15:84-87 (2005).

Han, G. et al., "Technetium Complexes for the Quantitation of Brain Amyloid," J. Am. Chem. Soc. 118:4506-4507 (1996).

Jicha, G.A. et al., "Neuropathologic outcome of mild cognitive impairment following progression to clinical dementia," Arch Neurol 63:674 (2006).

Hardy, J. "Has the amyloid cascade hypothesis for Alzheimer's disease been proved?" Curr Alzheimer Res 3:71 (2006).

Hardy, J. et al., "The amyloid hypothesis of Alzheimer's disease: progress and problems on the road to therapeutics," Science 297:353 (2002).

Hintersteiner, M. et al., "In vivo detection of amyloid-beta deposits by near-infrared imaging using an oxazine-derivative probe," Nat Biotechnol 23:577 (2005).

Hoffman, J.M. et al., "FDG PET imaging in patients with pathologically verified dementia," J Nucl Med 41:1920 (2000).

Huddleston, D.E. et al., "Technology Insight: imaging amyloid plaques in the living brain with positron emission tomography and MRI," Nat Clin Pract Neurol 1:96 (2005).

Ishii, K. et al., "PET is better than perfusion SPECT for early diagnosis of Alzheimer's disease—for," Eur J Nucl Med Mol Imaging 32:1463 (2005).

Kepe, V. et al. "Serotonin 1A receptors in the living brain of Alzheimer's disease patients," Proc Natl Acad Sci U S A 103:702 (2006).

Klunk, W.E. et al., "Quantitative evaluation of congo red binding to amyloid-like proteins with a beta-pleated sheet conformation," J. Histochem. Cytochem. 37:1273-1281 (1989).

Klunk, W.E. et al., "Chrysamine-G Binding to Alzheimer and Control Brain: Autopsy Study of a New Amyloid Probe," Neurobiol. Aging 16:541-548 (1995).

Klunk, W.E. et al., "Staining of AD and Tg2576 mouse brain with X-34, a highly fluorescent derivative of chrysamine G and a potential in vivo probe for β-sheet fibrils," Abstr. Soc. Neurosci. 23:1638, Abstract No. 636.12, Society for Neuroscience (1997).

Klunk, W.E. et al., "Binding of the positron emission tomography tracer Pittsburgh compound-B reflects the amount of amyloid-beta in Alzheimer's disease brain but not in transgenic mouse brain," J Neurosci 25:10598, (2005).

Klunk, W.E. et al., "Chrysamine-G, a lipophilic analogue of Congo red, inhibits Aβ-induced toxicity in PC12 cells," Life Sci 63:1807 (1998).

Klunk, W.E. et al., "Small-molecule beta-amyloid probes which distinguish homogenates of Alzheimer's and control brains," Biol Psychiatry 35:627 (1994).

Klunk, W.E. et al., "Uncharged thioflavin-T derivatives bind to amyloid-beta protein with high affinity and readily enter the brain," Life Sci 69:1471 (2001).

Kuner, P. et al., "Controlling Polymerization of β-Amyloid and Prion-derived Peptides with Synthetic Small Molecule Ligands," J. Biol. Chem. 275:1673-1678 (Jan. 2000).

Kung M-P. et al., "Binding of two potential imaging agents targeting amyloid plaques in postmortem brain tissues of patients with Alzheimer's disease," Brain Res. 1025:98-105 (2004).

Link, C.D. et al., "Visualization of fibrillar amyloid deposits in living, transgenic *Caenorhabditis elegans* animals using the sensitive amyloid dye, X-34," Neurobiol Aging 22:217 (2001).

Lopresti, B.J. et al., "Simplified Quantification of Pittsburgh Compound B Amyloid Imaging PET Studies: A Comparative Analysis," J Nucl Med 46:1959 (2005).

Lorenzo, A. et al., "Beta-amyloid neurotoxicity requires fibril formation and is inhibited by congo red," Proc. Natl. Acad. Sci. U.S.A. 91:12243-12247 (1994).

Marchesi, V.T., "An alternative interpretation of the amyloid Abeta hypothesis with regard to the pathogenesis of Alzheimer's disease," Proc Natl Acad Sci U S A 102:9093 (2005).

Mathis, C.A. et al., "Synthesis of a Lipophilic Radioiodinated Ligand with High Affinity to Amyloid Protein in Alzheimer's Disease Brain Tissue," Proc. Xllth Intl. Symp. Radiopharm. Chem., Uppsala, Sweden:94-95 (1997).

Mathis, C.A. et al., "A lipophilic thioflavin-T derivative for positron emission tomography (PET) imaging of amyloid in brain," Bioorg Med Chem Lett 12:295 (2002a).

Mathis, C.A. et al., "18F-labeled thioflavin-T analogs for amyloid assessment," J Nucl Med 43:166P, (2002b).

Mathis, C.A. et al., "Imaging technology for neurodegenerative diseases: progress toward detection of specific pathologies," Arch Neurol 62:196 (2005).

Mathis, C.A. et al., "Imaging b-amyloid plaques and neurofibrillary tangles in the aging human brain," Curr Pharm Des 10:1469 (2004).

Mega, M.S. et al., "Orbital and dorsolateral frontal perfusion defect associated with behavioral response to cholinesterase inhibitor therapy in Alzheimer's disease," J Neuropsychiatry Clin Neurosci 12:209 (2000a).

Mega, M.S. et al., "Cerebral correlates of psychotic symptoms in Alzheimer's disease," J Neurol Neurosurg Psychiatry 69:167 (2000b).

Minoshima, S. "Imaging Alzheimer's disease: clinical applications," Neuroimaging Clin N Am 13:769 (2003).

Minoshima, S. et al., "Metabolic reduction in the posterior cingulate cortex in very early Alzheimer's disease," Ann Neurol 42:85 (1997).

Mintun, M.A. et al., "[11C]PIB in a nondemented population: potential antecedent marker of Alzheimer disease," Neurology 67:446 (2006).

Moore, C.L. et al., "Difluoro ketone peptidomimetics suggest a large S1 pocket for Alzheimer's gamma-secretase: implications for inhibitor design," J. Med. Chem. 43:3434-3442 (2000).

Näslund, J. et al., "Correlation Between Elevated Levels of Amyloid β-Peptide in the Brain and Cognitive Decline," JAMA 283:1571-1577, American Medical Association (Mar. 2000).

Nesterov, E.E. et al., "In vivo optical imaging of amyloid aggregates in brain: design of fluorescent markers," Angew Chem Int Ed Engl 44:5452 (2005).

Nichols, L. et al., "Imaging and in vivo quantitation of beta-amyloid: an exemplary biomarker for Alzheimer's disease?" Biol Psychiatry 59:940 (2006).

Nordberg, A., "PET imaging of amyloid in Alzheimer's disease," Lancet Neurol 3:519-27 (2004).

Phelps, M.E., "PET: the merging of biology and imaging into molecular imaging," J Nucl Med 41:661 (2000).

Price, J.C. et al., "[O-15] Water and PIB PET imaging in Alzheimer's disease and mild cognitive impairment," J Nucl Med:75p (abstract) (2006).

Price, J.C. et al., "Kinetic modeling of amyloid binding in humans using PET imaging and Pittsburgh Compound-B," J Cereb Blood Flow Metab 25:1528 (2005).

Qu, W. et al., "Radioiodinated aza-diphenylacetylenes as potential SPECT imaging agents for β-amyloid plaque detection," Bioorganic & Medicinal Chemistry Letters, Jul. 1, 2007, 17(13), 3581-3584.

Rentz, D.M. et al., "Amyloid imaging in AD, MCI, and highly intelligent older adults with Pittsburgh Compound-B (PIB)," J Nucl Med:289p (abstract) (2006).

Rosenberg, R.N., "Explaining the cause of the amyloid burden in Alzheimer disease," Arch Neurol 59:1367 (2002).

Schmidt, B. et al., "Drug development and PET-diagnostics for Alzheimer's disease," Curr Med Chem 12:1677 (2005).

Selkoe, D.J., "Biology of β-amyloid Precursor Protein and the Mechanism of Alzheimer's Disease," Alzheimer's Disease, Lippincot Williams & Wilkins, Philadelphia, PA (1999), pp. 293-310.

Selkoe, D.J., "The Origins of Alzheimer Disease. A is for Amyloid," J. Am. Med. Assoc. 283:1615-1617 (2000).

Selkoe, D.J., "Alzheimer's disease: genes, proteins, and therapy," Physiol Rev 81:741 (2001).

Shoghi-Jadid, K. et al., "Localization of neurofibrillary tangles and beta-amyloid plaques in the brains of living patients with Alzheimer disease: Binding characteristics of radiofluorinated 6-dialkylamino-2-naphthylethylidene derivatives as positron emission tomography imaging probes for beta-amyloid plaques in Alzheimer disease," Am J Geriatr Psychiatry 10:24, (2002).

Shoghi-Jadid, K. et al., "Exploring a mathematical model for the kinetics of beta-amyloid molecular imaging probes through a critical analysis of plaque pathology," Mol Imaging Biol 8:151 (2006).

Shoghi-Jadid, K. et al.,"Imaging beta-amyloid fibrils in Alzheimer's disease: a critical analysis through simulation of amyloid fibril polymerization," Nucl Med Biol 32:337 (2005).

Silverman, D.H.S. et al., "Invited Commentary: Evaluating Dementia Using PET: How Do We Put into Clinical Perspective What We Know to Date?" J Nucl Med 41:1929 (2000).

Skovronsky, D.M. et al., "β-Secretase revealed: starting gate for race to novel therapies for Alzheimer's disease," Trends Pharmacol. Sci. 21:161-163 (2000).

Styren, S.D. et al., "X-34, a fluorescent derivative of Congo Red: a novel histochemical stain for Alzheimer's disease pathology," J Histochem Cytochem 48:1223 (2000).

Tang, B.N. et al., "Diagnosis of suspected Alzheimer's disease is improved by automated analysis of regional cerebral blood flow," Eur J Nucl Med Mol Imaging 31:1487 (2004).

Thal, D.R. et al., "The development of amyloid beta protein deposits in the aged brain," Sci Aging Knowledge Environ 2006:re1, (2006).

Vassar, R. et al., "β-Secretase Cleavage of Alzheimer's Amyloid Precursor Protein by the Transmembrane Aspartic Protease BACE," Science 286:735-741, 1999.

Verhoeff N.P. et al., "In-vivo imaging of Alzheimer disease beta-amyloid with [11C]SB-13 PET," Am J Geriatr Psychiatry. 12:584-95, (2004).

Villemagne, V.L. et al., "11C-PIB PET imaging in the differential diagnosis of dementia," J Nucl Med:74p (abstract), (2006).

Vogelsberg-Ragaglia, V. et al., "Cell Biology of Tau and Cytoskeletal Pathology in Alzheimer's Disease," Alzheimer's Disease, Lippincot, Williams & Wilkins, Philadelphia, PA (1999), pp. 359-372.

Wolfe, M.S. et al., "A substrate-based difluoro ketone selectively inhibits Alzheimer's gamma-secretase activity," J. Med. Chem. 41:6-9, 1998.

Xia, W. et al., "Presenilin complexes with the C-terminal fragments of amyloid precursor protein at the sites of amyloid beta-protein generation," J. Proc. Natl. Acad. Sci. U.S.A. 97:9299-9304, (2000).

Yang F. et al., "Curcumin inhibits formation of amyloid β oligomers and fibrils, binds plaques, and reduces amyloid in-vivo," J. Biol. Chem. 280:5892-5901, (2005).

Zhen, W. et al., "Synthesis and amyloid binding properties of rhenium complexes: preliminary progress toward a reagent for SPECT imaging of Alzheimer's disease brain," J. Med. Chem. 42:2805-2815 (1999).

* cited by examiner

| $K_i$ (nM) | $R^1$ | n | $K_i$ (nM) |
|---|---|---|---|
| 6.5 ± 0.9 | NMe₂ | 2 | 11 ± 0.8 |
| 6.6 ± 0.8 | NHMe | 3 | |

| $K_i$ (nM) | $R^1$ | $K_i$ (nM) | $R^1$ |
|---|---|---|---|
| 3.4 ± 1.1 | NMe₂ | 6.7 ± 1.3 | NMe₂ |
| 6.0 ± 1.1 | NHMe | 1.6 ± 0.5 | NHMe |
| | | 6.2 ± 1.2 | OH |

| | | | | | |
|---|---|---|---|---|---|
| X—⌬—≡—⌬—Y | | | X—⌬—≡—⌬—(O~)₃Z | | |
| $K_i$ (nM) | X | Y | $K_i$ (nM) | X | Z |
| 2.9 ± 0.4 | NO₂ | OMe | 21 ± 6.5 | NH₂ | F |
| 106 ± 6 | NH₂ | OH | 1.9 ± 0.3 | NHMe | F |
| 1.5 ± 0.1 | NHMe | OH | 2.9 ± 0.1 | NMe₂ | F |
| 1.6 ± 0.4 | NMe₂ | OH | 67.5 ± 7.5 | NH₂ | OH |
| 2.9 ± 0.3 | OMe | OH | 4.5 ± 0.9 | NHMe | OH |
| 175 ± 35 | H | H | 3.4 ± 0.1 | NMe₂ | OH |
| 76 ± 35 | NH₂ | NH₂ | 1.5 ± 0.4 | NMe₂ | OCH₂C≡CH |

Figure 4A

| Ki (nM) | X | A | B | n | Z |
|---|---|---|---|---|---|
| 2.9 | NMe₂ | C | H | 3 | F |
| 1.9 | NHMe | C | H | 3 | F |
| 5.0 | NMe₂ | N | H | 3 | F |
| 4.5 | NHMe | N | H | 3 | F |
| 3.2 | NMe₂ | N | H | 2 | F |
| 1.2 | NHMe | N | H | 2 | F |
| 6.6 | NHMe | N | I | 3 | F |
| 9.2 | NHMe₂ | N | I | 1 | OH |
| 17.2 | NHMe | N | I | 1 | OH |
| 2.8 | NHMe | N | I | 2 | OH |

| | | | | | |
|---|---|---|---|---|---|
| X—⟨phenyl⟩—C≡C—⟨phenyl(Br)⟩—Y | | | X—⟨phenyl⟩—C≡C—⟨pyridyl(Br)⟩—Z | | |
| $K_i$ (nM) | X | Y | $K_i$ (nM) | X | Z |
| 61.5 ± 6.5 | OH | NMe₂ | 1.6 ± 0.5 | NHMe | O∿OH |
| 15.2 ± 3.2 | OH | NHMe | 6.7 ± 0.3 | NMe₂ | O∿OH |
| 22.5 ± 2.5 | OH | OH | 90 ± 18 | NMe₂ | N∿OH |
| 38.5 ± 1.2 | NH₂ | OH | 8.5 ± 0.5 | NMe₂ | O∿O∿ |
| 5.2 ± 0.8 | NMe₂ | NHMe | 6.5 ± 0.9 | NHMe | O∿O∿ |
| 9.1 ± 0.9 | NMe₂ | N∿OH | | | |
| 3.4 ± 1.1 | NMe₂ | O∿OH | | | |
| 6.0 ± 1.1 | NHMe | O∿OH | | | |

Figure 5

| Compound | Ki | Compound | Ki | Compound | Ki |
|---|---|---|---|---|---|
| | 5.2±0.8 | | 16.8±1.8 | | 15.2±3.2 |
| | 1.2 | | | | 87.5±16 |
| | 3.4 | | 6.0 | | 33±4.5 |
| | 6.7±1.3 | | 1.6±0.5 | | 6.2±1.2 |
| | 9.2±1.7 | | 17±2.0 | | |
| | 9.1±0.9 | | 7.5 | | 22.5±2.5 |
| | 8.8±1.7 | | 6.6±0.9 | | 30±7.8 |
| | 90 | | 200 | | |
| | 6.6±0.9 | | 2.8±0.2 | | |
| | 8.5 | | 6.5 | | |
| | 11.2±0.8 | | 13.1±1.9 | | |

Figure 6

Mouse biodistribution and octanol/PBS partition coefficient (%dose/g, avg of 3 mice ± SD)

| Organ | 2 min | | 30 min | | 1 hr | | 2 hr | |
|---|---|---|---|---|---|---|---|---|
| Blood | 5.72 | ± 0.51 | 2.97 | ± 0.10 | 2.51 | ± 0.35 | 2.35 | ± 0.39 |
| Heart | 9.97 | ± 1.51 | 1.49 | ± 0.14 | 1.04 | ± 0.07 | 0.84 | ± 0.10 |
| Muscle | 0.79 | ± 0.24 | 0.67 | ± 0.10 | 0.51 | ± 0.08 | 0.42 | ± 0.05 |
| Lung | 8.38 | ± 1.28 | 2.26 | ± 0.25 | 1.26 | ± 0.90 | 1.47 | ± 0.19 |
| Kidney | 12.37 | ± 2.37 | 2.68 | ± 0.08 | 2.53 | ± 0.21 | 2.02 | ± 0.50 |
| Spleen | 4.61 | ± 0.76 | 1.39 | ± 0.14 | 1.13 | ± 0.07 | 1.17 | ± 0.17 |
| Liver | 23.19 | ± 3.53 | 13.79 | ± 0.92 | 8.13 | ± 1.69 | 6.58 | ± 0.43 |
| Skin | 0.68 | ± 0.17 | 1.41 | ± 0.24 | 1.28 | ± 0.06 | 0.68 | ± 0.18 |
| Brain | 6.78 | ± 1.16 | 1.57 | ± 0.13 | 0.77 | ± 0.07 | 0.42 | ± 0.03 |
| Bone | 1.51 | ± 0.34 | 0.64 | ± 0.04 | 0.56 | ± 0.10 | 0.70 | ± 0.11 |

Partition coefficient      1538  (taken from third partition)

Mouse biodistribution and octanol/PBS partition coefficient

(%dose/g, avg of 3 mice ± SD)

| Organ | 2 min | | 30 min | | 1 hr | | 2 hr | |
|---|---|---|---|---|---|---|---|---|
| Blood | 3.28 | ± 0.63 | 3.28 | ± 0.57 | 3.22 | ± 0.19 | 3.17 | ± 0.62 |
| Heart | 4.21 | ± 0.79 | 1.40 | ± 0.17 | 1.24 | ± 0.19 | 0.96 | ± 0.19 |
| Muscle | 1.97 | ± 1.15 | 0.61 | ± 0.10 | 0.62 | ± 0.07 | 0.39 | ± 0.14 |
| Lung | 4.64 | ± 0.76 | 2.10 | ± 0.30 | 2.04 | ± 0.28 | 1.72 | ± 0.27 |
| Kidney | 4.74 | ± 1.22 | 2.90 | ± 0.99 | 2.40 | ± 0.22 | 1.80 | ± 0.62 |
| Spleen | 2.69 | ± 0.60 | 1.22 | ± 0.04 | 0.95 | ± 0.04 | 1.02 | ± 0.15 |
| Liver | 25.80 | ± 2.80 | 14.75 | ± 4.12 | 10.16 | ± 4.00 | 9.14 | ± 3.24 |
| Skin | 1.24 | ± 0.29 | 1.40 | ± 0.23 | 0.95 | ± 0.11 | 0.60 | ± 0.17 |
| Brain | 4.55 | ± 0.82 | 0.42 | ± 0.13 | 0.37 | ± 0.02 | 0.38 | ± 0.07 |
| Bone | 1.50 | ± 0.16 | 0.66 | ± 0.12 | 0.65 | ± 0.09 | 0.82 | ± 0.15 |

Partition coefficient      1182 (taken from third partition)

Mouse biodistribution and octanol/PBS partition coefficient

%dose/g

| Organ | 2 min | 30 min | 60 min | 120 min |
|---|---|---|---|---|
| Blood | 10.27 ± 2.36 | 5.11 ± 0.64 | 3.34 ± 0.94 | 2.19 ± 0.35 |
| Heart | 11.28 ± 4.77 | 5.08 ± 0.61 | 4.19 ± 3.53 | 2.65 ± 0.23 |
| Muscle | 1.52 ± 0.50 | 0.85 ± 0.04 | 0.68 ± 0.11 | 0.60 ± 0.18 |
| Lung | 6.57 ± 1.24 | 3.79 ± 0.52 | 2.77 ± 0.61 | 2.17 ± 0.19 |
| Kidney | 7.73 ± 1.77 | 5.12 ± 0.83 | 3.38 ± 0.55 | 2.73 ± 0.63 |
| Spleen | 6.05 ± 1.26 | 5.72 ± 1.60 | 4.26 ± 0.21 | 5.40 ± 0.56 |
| Liver | 19.79 ± 6.71 | 16.09 ± 3.16 | 10.42 ± 2.20 | 10.87 ± 0.43 |
| Skin | 0.90 ± 0.30 | 1.07 ± 0.15 | 0.90 ± 0.07 | 0.76 ± 0.21 |
| Brain | 1.06 ± 0.20 | 0.53 ± 0.11 | 0.24 ± 0.07 | 0.16 ± 0.02 |
| Thyroid | 5.70 ± 2.77 | 7.52 ± 1.75 | 28.27 ± 11.65 | 77.20 ± 0.38 |

P. C. 368 taken from third partition of octanol/0.05 M $Na_2HPO_4$ - buffer (pH 7.4)

Mouse biodistribution

| Organ | 2 min | | 30 min | | 1 hr | | 2 hr | |
|---|---|---|---|---|---|---|---|---|
| Blood | 3.45 | ± 0.29 | 3.38 | ± 0.51 | 2.71 | ± 0.43 | 3.29 | ± 0.61 |
| Heart | 12.96 | ± 2.47 | 2.31 | ± 0.37 | 1.41 | ± 0.33 | 1.33 | ± 0.26 |
| Muscle | 0.98 | ± 0.30 | 1.23 | ± 0.20 | 0.71 | ± 0.09 | 0.78 | ± 0.11 |
| Lung | 13.03 | ± 2.32 | 4.03 | ± 0.41 | 2.60 | ± 0.56 | 2.77 | ± 0.86 |
| Kidney | 16.63 | ± 2.48 | 4.10 | ± 0.54 | 2.85 | ± 0.50 | 2.40 | ± 0.47 |
| Spleen | 6.33 | ± 1.03 | 1.98 | ± 0.34 | 1.42 | ± 0.40 | 1.73 | ± 0.45 |
| Liver | 17.16 | ± 2.86 | 11.25 | ± 1.59 | 5.21 | ± 2.05 | 2.24 | ± 0.45 |
| Skin | 0.87 | ± 0.14 | 2.22 | ± 0.64 | 2.46 | ± 0.27 | 3.18 | ± 0.17 |
| Brain | 5.67 | ± 1.49 | 4.51 | ± 0.56 | 2.14 | ± 0.21 | 0.91 | ± 0.17 |

ACETYLENE DERIVATIVES AND THEIR USE FOR BINDING AND IMAGING AMYLOID PLAQUES

CROSS-REFERENCE TO RELATED APPLICATIONS

This applications claims the benefit of U.S. Provisional Application No. 60/873,249, filed Dec. 7, 2006, which is incorporated herein by reference, in its entirety.

GOVERNMENT RIGHTS

Pursuant to 35 U.S.C. §202(c), it is acknowledged that the United States Government may have rights in the invention described herein, which was made in part with funding from the National Institutes of Health through Grants AG-21868 and AG-22559.

FIELD OF THE INVENTION

This invention relates to novel bioactive compounds, methods of diagnostic imaging using radiolabeled compounds, and methods of making radiolabeled compounds.

BACKGROUND OF THE INVENTION

Alzheimer's disease (AD) is a progressive neurodegenerative disorder characterized by cognitive decline, irreversible memory loss, disorientation, and language impairment. Alzheimer's disease (AD) is a common neurodegenerative disease of the brain. It is a significant medical problem with a high prevalence in millions of elder people. Major neuropathology observations of postmortem AD brains depict the presence of senile plaques (containing β-amyloid (Aβ) aggregates) and neurofibrillary tangles (highly phosphorylated tau proteins). Currently, there is no definitive imaging method to diagnose AD, except by postmortem biopsy and staining of the brain tissue which demonstrates the senile plaques containing predominantly Aβ aggregates.

Several genomic factors have been linked to AD. Familial AD (or early onset AD) has been reported to have mutations in genes encoding β-amyloid precursor protein (APP), presenilin 1 (PS1) and presenilin 2 (PS2) (Berezovska, O, A Lleo, L D Herl, et al. "Familial Alzheimer's disease presenilin 1 mutations cause alterations in the conformation of presenilin and interactions with amyloid precursor protein." *J Neurosci* 25:3009 (2005); Deng, Y, L Tarassishin, V Kallhoff, et al. "Deletion of presenilin 1 hydrophilic loop sequence leads to impaired gamma-secretase activity and exacerbated amyloid pathology." *J Neurosci* 26:3845 (2006); Hardy, J, D J Selkoe "The amyloid hypothesis of Alzheimer's disease: progress and problems on the road to therapeutics." *Science* 297:353 (2002); Selkoe, D J "Alzheimer's disease: genes, proteins, and therapy." *Physiol Rev* 81:741 (2001)). The exact mechanisms of these mutations which lead to the development of AD are not fully understood; however, the formation of Aβ plaques in the brain is a pivotal event in the pathology of Alzheimer's disease.

Amyloidosis is a condition characterized by the accumulation of various insoluble, fibrillar proteins in the tissues of a patient. An amyloid deposit is formed by the aggregation of amyloid proteins, followed by the further combination of aggregates and/or amyloid proteins. Formation of soluble and diffusible Aβ and Aβ aggregates in the brain are now considered the critical events, which produce various toxic effects in neuronal cells leading to the formation of neuritic plaques (Catalano, S M, E C Dodson, D A Henze, et al. "The Role of Amyloid-Beta Derived Diffusible Ligands (ADDLs) in Alzheimer's Disease." *Curr Top Med Chem* 6:597 (2006); Hardy, (2002); Jicha, G A, J E Parisi, D W Dickson, et al. "Neuropathologic outcome of mild cognitive impairment following progression to clinical dementia." *Arch Neurol* 63:674 (2006); Rosenberg, R N "Explaining the cause of the amyloid burden in Alzheimer disease." *Arch Neurol* 59:1367 (2002); Thal, D R, E Capetillo-Zarate, K Del Tredici, et al. "The development of amyloid beta protein deposits in the aged brain." *Sci Aging Knowledge Environ* 2006:re1, (2006)). Recent reports have suggested that β-amyloid aggregates, i.e. Aβ plaques, in the brain play a key role in a cascade of events leading to AD. Postmortem examination of AD brain sections reveals abundant senile plaques (SPs) composed of amyloid-β (Aβ) peptides and numerous neurofibrillary tangles (NFTs) formed by filaments of highly phosphorylated tau proteins (for recent reviews and additional citations see Ginsberg, S. D., et al., "Molecular Pathology of Alzheimer's Disease and Related Disorders," in *Cerebral Cortex: Neurodegenerative and Age-related Changes in Structure and Function of Cerebral Cortex*, Kluwer Academic/Plenum, NY (1999), pp. 603-654; Vogelsberg-Ragaglia, V., et al., "Cell Biology of Tau and Cytoskeletal Pathology in Alzheimer's Disease," *Alzheimer's Disease*, Lippincot, Williams & Wilkins, Philadelphia, Pa. (1999), pp. 359-372).

While the exact mechanisms underlying AD are not fully understood, all pathogenic familial AD (FAD) mutations studied thus far increase production of the more amyloidogenic 42-43 amino-acid long form of the Aβ peptide. Thus, at least in FAD, dysregulation of Aβ production appears to be sufficient to induce a cascade of events leading to neurodegeneration. Indeed, the amyloid cascade hypothesis suggests that formation of extracellular fibrillar Aβ aggregates in the brain may be a pivotal event in AD pathogenesis (Selkoe, D. J., "Biology of β-amyloid Precursor Protein and the Mechanism of Alzheimer's Disease," *Alzheimer's Disease*, Lippincot Williams & Wilkins, Philadelphia, Pa. (1999), pp. 293-310; Selkoe, D. J., *J. Am. Med. Assoc.* 283:1615-1617 (2000); Naslund, J., et al., *J. Am. Med. Assoc.* 283:1571-1577, (2000); Golde, T. E., et al., *Biochimica et Biophysica Acta* 1502:172-187 (2000)).

Significant circumstantial evidence suggests that fibrillary Aβ plaques consisting predominately of aggregates of Aβ$_{40}$ and Aβ$_{42}$ peptides play a major role in AD pathogenesis —"Amyloid Cascade Hypothesis" (Armstrong, R A "Plaques and tangles and the pathogenesis of Alzheimer's disease." *Folia Neuropathol* 44:1 (2006); Golde, T E "The Abeta hypothesis: leading us to rationally-designed therapeutic strategies for the treatment or prevention of Alzheimer disease." *Brain Pathol* 15:84 (2005); Hardy, J "Has the amyloid cascade hypothesis for Alzheimer's disease been proved?" *Curr Alzheimer Res* 3:71 (2006); Hardy (2002); Marchesi, V T "An alternative interpretation of the amyloid Abeta hypothesis with regard to the pathogenesis of Alzheimer's disease." *Proc Natl Acad Sci USA* 102:9093 (2005)). ApoE4 expression appears to increase the risk of AD (Fryer, J D, J W Taylor, R B DeMattos, et al. "Apolipoprotein E markedly facilitates age-dependent cerebral amyloid angiopathy and spontaneous hemorrhage in amyloid precursor protein transgenic mice." *J Neurosci* 23:7889 (2003)). It is likely that amyloid precursor protein (APP) is degraded by several proteases, among which the catabolism reactions of β- and β-secretases on APP lead to the production of excess Aβ. The excessive burden of Aβ, produced by various normal or abnormal mechanisms, may represent the starting point of neurodegenerative events. The fibrillar aggregates of amyloid peptides, Aβ$_{40}$ and Aβ$_{42}$, are major metabolic peptides derived from amyloid precursor protein found in senile plaques and cerebrovascular amyloid deposits in AD patients (Xia, W., et al., *J. Proc. Natl. Acad. Sci. U.S.A.* 97:9299-9304, (2000)). Prevention and reversal of Aβ plaque formation are being targeted as a treatment for this disease (Selkoe, D., J. JAMA 283:1615-1617 (2000); Wolfe, M. S., et al., J. Med. Chem. 41:6-9, 1998; Skovronsky, D. M., and Lee, V. M., *Trends Pharmacol. Sci.* 21:161-163 (2000)).

Early appraisal of clinical symptoms for diagnosis of AD is often difficult and unreliable (Boss, M A "Diagnostic approaches to Alzheimer's disease." *Biochim Biophys Acta* 1502:188 (2000)). Positron emission tomography (PET) and single photon emission tomography (SPECT) imaging of regional cerebral blood flow (rCBF) for diagnosis and monitoring of patients with AD have been reported (Ishii, K, S Minoshima "PET is better than perfusion SPECT for early diagnosis of Alzheimer's disease—for." *Eur J Nucl Med Mol Imaging* 32:1463 (2005); Mega, M S, I D Dinov, L Lee, et al. "Orbital and dorsolateral frontal perfusion defect associated with behavioral response to cholinesterase inhibitor therapy in Alzheimer's disease." *J Neuropsychiatry Clin Neurosci* 12:209 (2000a); Mega, M S, L Lee, I D Dinov, et al. "Cerebral correlates of psychotic symptoms in Alzheimer's disease." *J Neurol Neurosurg Psychiatry* 69:167 (2000b); Tang, B N, S Minoshima, J George, et al. "Diagnosis of suspected Alzheimer's disease is improved by automated analysis of regional cerebral blood flow." *Eur J Nucl Med Mol Imaging* 31:1487 (2004)). Diagnosis of AD based on regional glucose metabolism in the brain has been evaluated using PET imaging with [$^{18}$F]2-fluoro-2-deoxyglucose (FDG). The overall performance of FDG/PET is favorable for routine clinical evaluation of suspected AD (Frey, K A, S Minoshima, D E Kuhl "Neurochemical imaging of Alzheimer's disease and other degenerative Dementias." *Q J Nucl Med* 42:166 (1998); Hoffman, J M, K A Welsh-Bohmer, M Hanson, et al. "FDG PET imaging in patients with pathologically verified dementia." *J Nucl Med* 41:1920 (2000); Minoshima, S "Imaging Alzheimer's disease: clinical applications." *Neuroimaging Clin N Am* 13:769 (2003); Minoshima, S, B Giordani, S Berent, et al. "Metabolic reduction in the posterior cingulate cortex in very early Alzheimer's disease." *Ann Neurol* 42:85 (1997); Phelps, M E "PET: the merging of biology and imaging into molecular imaging." *J Nucl Med* 41:661 (2000); Silverman, D H S, M E Phelps "Invited Commentary: Evaluating Dementia Using PET: How Do We Put into Clinical Perspective What We Know to Date?" *J Nucl Med* 41:1929 (2000)). While imaging rCBF and glucose metabolism may have some use in AD patients, none of these modalities provide any information on the presence or quantity of Aβ aggregates in the brain.

Various approaches in trying to inhibit the production and reduce the accumulation of fibrillar Aβ in the brain are currently being evaluated as potential therapies for AD (Skovronsky, D. M. and Lee, V. M., *Trends Pharmacol. Sci.* 21:161-163 (2000); Vassar, R., et al., *Science* 286:735-741, 1999; Wolfe, M. S., et al., *J. Med. Chem.* 41:6-9, 1998; Moore, C. L., et al., *J. Med. Chem.* 43:3434-3442 (2000); Findeis, M. A., *Biochimica et Biophysica Acta* 1502:76-84, 2000; Kuner, P., Bohrmann, et al., *J. Biol. Chem.* 275:1673-1678 (2000)). It is therefore of interest to develop ligands that specifically bind fibrillar Aβ aggregates. Since extracellular SPs are accessible targets, these new ligands could be used as in vivo diagnostic tools and as probes to visualize the progressive deposition of Aβ in studies of AD amyloidogenesis in living patients. Development of Aβ plaque-specific imaging agents has been reported previously (for review see Blennow, K, H Zetterberg "Pinpointing plaques with PIB." *Nat Med* 12:753 (2006b); Huddleston, D E, S A Small "Technology Insight: imaging amyloid plaques in the living brain with positron emission tomography and MRI." *Nat Clin Pract Neurol* 1:96 (2005); Mathis, C A, Y Wang, W E Klunk "Imaging b-amyloid plaques and neurofibrillary tangles in the aging human brain." *Curr Pharm Des* 10:1469 (2004); Nichols, L, VW Pike, L Cai, et al. "Imaging and in vivo quantitation of beta-amyloid: an exemplary biomarker for Alzheimer's disease?" *Biol Psychiatry* 59:940 (2006); Schmidt, B, HA Braun, R Narlawar "Drug development and PET-diagnostics for Alzheimer's disease." *Curr Med Chem* 12:1677 (2005)).

Potential ligands for detecting Aβ aggregates in the living brain must cross the intact blood-brain barrier. Thus brain uptake can be improved by using ligands with relatively smaller molecular size and increased lipophilicity. Highly conjugated thioflavins (S and T) are commonly used as dyes for staining the Aβ aggregates in the AD brain (Elhaddaoui, A., et al., Biospectroscopy 1:351-356 (1995)). To this end, several interesting approaches for developing fibrillar Aβ aggregate-specific ligands have been reported (Ashburn, T. T., et al., *Chem. Biol.* 3:351-358 (1996); Han, G., et al., *J. Am. Chem. Soc.* 118:4506-4507 (1996); Klunk, W. E., et al., *Biol. Psychiatry* 35:627 (1994); Klunk, W. E., et al., *Neurobiol. Aging* 16:541-548 (1995); Klunk, W. E., et al., Society for Neuroscience Abstract 23:1638 (1997); Mathis, C. A., et al., *Proc. XIIth Intl. Symp. Radiopharm. Chem., Uppsala, Sweden:*94-95 (1997); Lorenzo, A. and Yankner, B. A., *Proc. Natl. Acad. Sci. U.S.A.* 91:12243-12247 (1994); Zhen, W., et al., *J. Med. Chem.* 42:2805-2815 (1999); Klunk, W. E., et al., *J. Histochem. Cytochem.* 37:1273-1281 (1989)).

The approach has been based on highly conjugated dyes, such as Congo Red and Chrysamine G (CG) (Dezutter, N A, R J Dom, T J de Groot, et al. "$^{99m}$Tc-MAMA-chrysamine G, a probe for beta-amyloid protein of Alzheimer's disease." *Eur J Nucl Med* 26:1392 (1999); Klunk, W E, M L Debnath, A M Koros, et al. "Chrysamine-G, a lipophilic analogue of Congo red, inhibits Aβ-induced toxicity in PC12 cells." *Life Sci* 63:1807 (1998); Klunk, W E, M L Debnath, J W Pettegrew "Small-molecule beta-amyloid probes which distinguish homogenates of Alzheimer's and control brains." *Biol Psychiatry* 35:627 (1994)). Thioflavin S and T have also been used in fluorescent staining of plaques and tangles in post-mortem AD brain sections (Elhaddaoui, A, E Pigorsch, A Delacourte, et al. "Competition of congo red and thioflavin S binding to amyloid sites in Alzheimer's diseased tissue." *Biospectroscopy* 1:351 (1995)). More abbreviated forms of Chrysamine G (CG), such as styrylbenzenes, have been reported as fluorescent dyes for staining amyloid aggregates (Link, C D, C J Johnson, V Fonte, et al. "Visualization of fibrillar amyloid deposits in living, transgenic *Caenorhabditis elegans* animals using the sensitive amyloid dye, X-34." *Neurobiol Aging* 22:217 (2001); Styren, S D, R L Hamilton, G C Styren, et al. "X-34, a fluorescent derivative of Congo Red: a novel histochemical stain for Alzheimer's disease pathology." *J Histochem Cytochem* 48:1223 (2000)). They are useful research tools but these charged and bulky agents do not cross intact blood-brain barrier.

A highly lipophilic tracer, [$^{18}$F]FDDNP, for binding both tangles (mainly composed of hyperphosphorylated tau protein) and plaques (containing Aβ protein aggregates) has been reported. (Shoghi-Jadid K, et al., *Am J Geriatr Psychiatry.* 10:24-35 (2002); Barrio, J R, S- C Huang, G Cole, et al. "PET imaging of tangles and plaques in Alzheimer's disease with a highly hydrophobic probe." *J Lab Compds Radiopharm* 42 Suppl. 1:S194, (1999a); Barrio, J R, S C Huang, G M Cole, et al. "PET imaging of tangles and plaques in Alzheimer's disease." *J Nucl Med* 40:70P, (1999b)). Preliminary studies in humans suggested that [$^{18}$F]FDDNP showed a higher retention in regions of brain suspected of having tangles and plaques (Kepe, V, J R Barrio, S C Huang, et al. "Serotonin 1A receptors in the living brain of Alzheimer's disease patients." *Proc Natl Acad Sci USA* 103:702 (2006); Shoghi-Jadid, K, J R Barrio, V Kepe, et al. "Exploring a mathematical model for the kinetics of beta-amyloid molecular imaging probes through a critical analysis of plaque pathology." *Mol Imaging Biol* 8:151 (2006); Shoghi-Jadid, K, J R Barrio, V Kepe, et al. "Imaging beta-amyloid fibrils in Alzheimer's disease: a critical analysis through simulation of amyloid fibril polymerization." Nucl Med Biol 32:337 (2005); Shoghi-Jadid, K, G W Small, E D Agdeppa, et al. "Localization of neurofibrillary tangles and beta-amyloid plaques in the brains of living patients with Alzheimer disease: Binding characteristics of radiofluorinated 6-dialkylamino-2-naphthylethylidene derivatives as positron emission tomography imaging probes for beta-amyloid plaques in Alzheimer disease." *Am J Geriatr Psychiatry* 10:24, (2002)). Using positron-emission tomography (PET), it was reported that this tracer specifically labeled deposits of plaques and tangles in nine AD patients and seven comparison subjects. (Nordberg A. *Lancet Neurol.* 3:519-27 (2004)). Using a novel pharmacokinetic analysis procedure called the relative residence time of the brain region of interest versus the pons, differences between AD patients and comparison subjects were demonstrated. The relative residence time was significantly higher in AD patients. This is further complicated by an intriguing finding that FDDNP competes with some NSAIDs for binding to Aβ fibrils in vitro and to Aβ plaques ex vivo (Agdeppa E D, et al. 2001; Agdeppa E D, et al., *Neuroscience.* 2003; 117:723-30).

A neutral and lipophilic thioflavin derivative, [$^{11}$C]6-OH-BTA-1 (PIB), showed excellent brain penetration and initial brain uptake, and displayed a high binding affinity to Aβ plaques ($K_i$=2.8 nM) (Klunk, W E, Y Wang, G- f Huang, et al. "Uncharged thioflavin-T derivatives bind to amyloid-beta protein with high affinity and readily enter the brain." *Life Sci* 69:1471 (2001); Mathis, C A, B J Bacskai, STBMC Kajdasz, et al. "A lipophilic thioflavin-T derivative for positron emission tomography (PET) imaging of amyloid in brain." *Bioorg Med Chem Lett* 12:295 (2002a); Mathis, C A, Y Wang, W E Klunk "Imaging b-amyloid plaques and neurofibrillary tangles in the aging human brain." *Curr Pharm Des* 10:1469 (2004); (Mathis C A, et al., *Curr Pharm Des.* 10:1469-92 (2004); Mathis C A, et al., *Arch. Neurol.* 62:196-200 (2005)). Contrary to that observed for [$^{18}$F]FDDNP, [$^{11}$C]6-OH-BTA-1 binds specifically to fibrillar Aβ in vivo. Patients with diagnosed mild AD showed marked retention of [$^{11}$C]6-OH-BTA-1 in the cortex, known to contain large amounts of amyloid deposits in AD. In the AD patient group, [$^{11}$C6]-OH-BTA-1 retention was increased most prominently in the frontal cortex. Large increases also were observed in parietal, temporal, and occipital cortices and in the striatum. [$^{11}$C]6-OH-BTA-1 retention was equivalent in AD patients and comparison subjects in areas known to be relatively unaffected by amyloid deposition (such as subcortical white matter, pons, and cerebellum). Fluorinated PIB and related neutral thioflavin derivatives, such as BTA-1, have also been reported (Mathis, C A, D P Holt, Y Wang, et al. "$^{18}$F-labeled thioflavin-T analogs for amyloid assessment." *J Nucl Med* 43:166P, (2002b)).

In the past few years, successful PET imaging studies in AD patients with [$^{11}$C]PIB has been reported (Klunk, W E, B J Lopresti, M D Ikonomovic, et al. "Binding of the positron emission tomography tracer Pittsburgh compound-B reflects the amount of amyloid-beta in Alzheimer's disease brain but not in transgenic mouse brain." *J Neurosci* 25:10598, (2005); Lopresti, B J, W E Klunk, C A Mathis, et al. "Simplified Quantification of Pittsburgh Compound B Amyloid Imaging PET Studies: A Comparative Analysis." *J Nucl Med* 46:1959 (2005); Mathis, C A, W E Klunk, J C Price, et al. "Imaging technology for neurodegenerative diseases: progress toward detection of specific pathologies." *Arch Neurol* 62:196 (2005); Price, J C, W E Klunk, B J Lopresti, et al. "Kinetic modeling of amyloid binding in humans using PET imaging and Pittsburgh Compound-B." *J Cereb Blood Flow Metab* 25:1528 (2005)). Recently, [$^{11}$C]PIB has been used in testing a limited number of patients with mild cognitive impairment (MCI) (Buckner, R L, A Z Snyder, B J Shannon, et al. "Molecular, structural, and functional characterization of Alzheimer's disease: evidence for a relationship between default activity, amyloid, and memory." *J Neurosci* 25:7709 (2005); Nordberg, A "PET imaging of amyloid in Alzheimer's disease." *Lancet Neurol* 3:519 (2004); Price, J C, W E Klunk, B J Lopresti, et al. "Kinetic modeling of amyloid binding in humans using PET imaging and Pittsburgh Compound-B." *J Cereb Blood Flow Metab* 25:1528, (2005)). Using PIB/PET to study the relationship between Aβ plaque burden and AD neurological measurements, the results seem to suggest that there are some MC1 cases that convert to AD, while those with lower PIB uptake in the cortex appear to have less propensity to convert to AD (Engler, H, A Forsberg, O Almkvist, et al. "Two-year follow-up of amyloid deposition in patients with Alzheimer's disease." *Brain* (2006); Mintun, M A, G N Larossa, Y I Sheline, et al. "[$^{11}$C]PIB in a nondemented population: potential antecedent marker of Alzheimer disease." *Neurology* 67:446 (2006); Price, J C, S K Ziolko, L A Weissfeld, et al. "[O-15] Water and PIB PET imaging in Alzheimer's disease and mild cognitive impairment." *J Nucl Med:*75p (abstract) (2006); Rentz, D M, J A Becker, E Moran, et al. "Amyloid imaging in AD, MCI, and highly intelligent older adults with Pittsburgh Compound-B (PIB)." *J Nucl Med:*289p (abstract) (2006); Villemagne, V L, S Ng, S J Gong, et al. "$^{11}$C-PIB PET imaging in the differential diagnosis of dementia." *J Nucl Med:*74p (abstract), (2006)).

Recently, another $^{11}$C labeled Aβ plaque-targeting probe, a stilbene derivative, [$^{11}$C]SB-13, has been studied. In vitro binding using the [$^{3}$H]SB-13 suggests that the compound showed excellent binding affinity and binding can be clearly measured in the cortical gray matter, but not in the white matter of AD cases. (Kung M-P, et al., *Brain Res.* 1025:98-105 (2004). There was a very low specific binding in cortical tissue homogenates of control brains. The $K_d$ values of [$^{3}$H] SB-13 in AD cortical homogenates were 2.4±0.2 nM. High binding capacity and comparable values were observed (14-45 pmol/mg protein) (Id.). As expected, in AD patients [$^{11}$C] SB-13 displayed a high accumulation in the frontal cortex (presumably an area containing a high density of Aβ plaques) in mild to moderate AD patients, but not in age-matched control subjects. (Verhoeff N P, et al., *Am J Geriatr Psychiatry.* 12:584-95, (2004)).

Recently, there have been reports on using an in vivo multiphoton optical imaging technique for invasive imaging of senile plaques in transgenic mice (by opening the skull) (Bacskai, B J, S T Kajdasz, R H Christie, et al. "Imaging of amyloid-beta deposits in brains of living mice permits direct observation of clearance of plaques with immunotherapy." Nat Med 7:369, (2001)). Additional improvements on developing near-infrared optical imaging agents have been reported (Bacskai, B J, G A Hickey, J Skoch, et al. "Four-dimensional multiphoton imaging of brain entry, amyloid binding, and clearance of an amyloid-beta ligand in transgenic mice." *Proc Natl Acad Sci USA* 100:12462 (2003); Hintersteiner, M, A Enz, P Frey, et al. "In vivo detection of amyloid-beta deposits by near-infrared imaging using an oxazine-derivative probe." *Nat Biotechnol* 23:577 (2005); Nesterov, E E, J Skoch, B T Hyman, et al. "In vivo optical imaging of amyloid aggregates in brain: design of fluorescent markers." *Angew Chem Int Ed Engl* 44:5452 (2005)).

There are several potential benefits of imaging Aβ aggregates in the brain. The imaging technique will improve diagnosis by identifying potential patients with excess Aβ plaques in the brain; therefore, they may be likely to develop Alzheimer's disease. It will also be useful to monitor the progression of the disease. When anti-plaque drug treatments become available, imaging Aβ plaques in the brain may provide an essential tool for monitoring treatment. Thus, a simple, noninvasive method for detecting and quantitating amyloid deposits in a patient has been eagerly sought. Presently, detection of amyloid deposits involves histological analysis of biopsy or autopsy materials. Both methods have drawbacks. For example, an autopsy can only be used for a postmortem diagnosis.

In addition to the role of amyloid deposits in Alzheimer's disease, the presence of amyloid deposits has been shown in diseases such as Mediterranean fever, Muckle-Wells syndrome, idiopathetic myeloma, amyloid polyneuropathy, amyloid cardiomyopathy, systemic senile amyloidosis, amyloid polyneuropathy, hereditary cerebral hemorrhage with amyloidosis, Down's syndrome, Scrapie, Creutzfeldt-Jacob disease, Kuru, Gerstamnn-Straussler-Scheinker syndrome, medullary carcinoma of the thyroid, Isolated atrial amyloid, $\beta_2$-microglobulin amyloid in dialysis patients, inclusion body myositis, $\beta_2$-amyloid deposits in muscle wasting disease, and Islets of Langerhans diabetes Type II insulinoma.

The direct imaging of amyloid deposits in vivo is difficult, as the deposits have many of the same physical properties (e.g., density and water content) as normal tissues. Attempts to image amyloid deposits using magnetic resonance imaging (MRI) and computer-assisted tomography (CAT) have been disappointing and have detected amyloid deposits only under certain favorable conditions. In addition, efforts to label amyloid deposits with antibodies, serum amyloid P protein, or other probe molecules have provided some selectivity on the periphery of tissues, but have provided for poor imaging of tissue interiors.

It would be useful to have a noninvasive technique for imaging and quantitating amyloid deposits in a patient. In addition, it would be useful to have compounds that inhibit the aggregation of amyloid proteins to form amyloid deposits and a method for determining a compound's ability to inhibit amyloid protein aggregation.

SUMMARY OF THE INVENTION

The present invention provides novel compounds of Formulas I and II.

The present invention also provides diagnostic compositions comprising a radiolabeled compound of Formula I or II and a pharmaceutically acceptable carrier or diluent.

The invention further provides a method of imaging amyloid deposits, the method comprising introducing into a mammal a detectable quantity of a labeled compound of Formula I or II or a pharmaceutically acceptable salt, ester, amide or prodrug thereof.

The present invention also provides a method for inhibiting the aggregation of amyloid proteins, the method comprising administering to a mammal an amyloid inhibiting amount of a compound Formulas I and II or a pharmaceutically acceptable salt, ester, amide, or prodrug thereof.

A further aspect of this invention is directed to methods and intermediates useful for synthesizing the amyloid inhibiting and imaging compounds of Formula I or II described herein.

BRIEF DESCRIPTION OF THE DRAWINGS

FIG. 1 depicts $K_i$ binding data of preferred compounds of the present invention.

FIGS. 4A, 4B, 5 and 6 depict $K_i$ in vitro binding data of several compounds of the invention.

DETAILED DESCRIPTION OF ILLUSTRATIVE EMBODIMENTS

Figure 2:
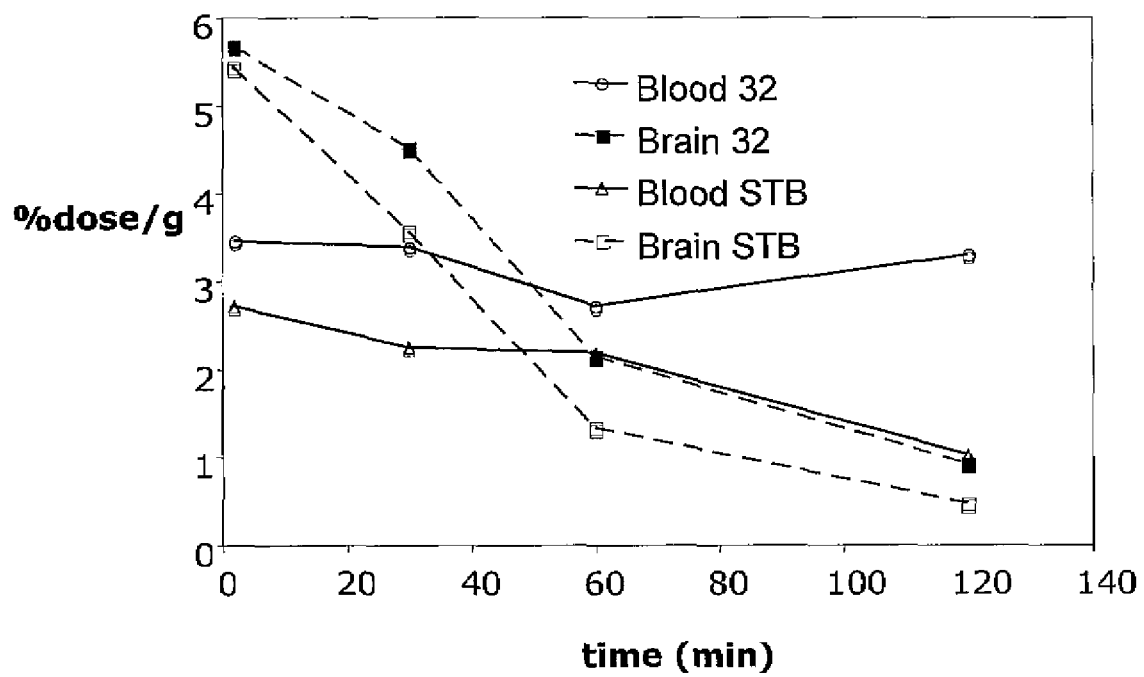
FIG. 2 depicts in vivo brain penetration of a preferred compound of the present invention. The presence of the compound was evaluated after iv injection in normal mice.
Figure 2:
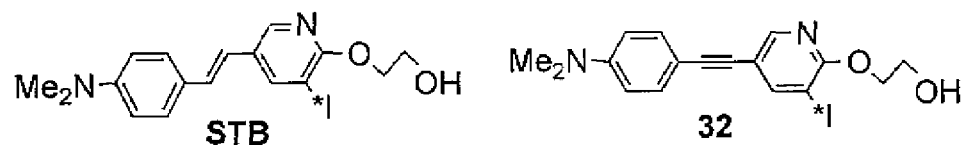
Figure 3:
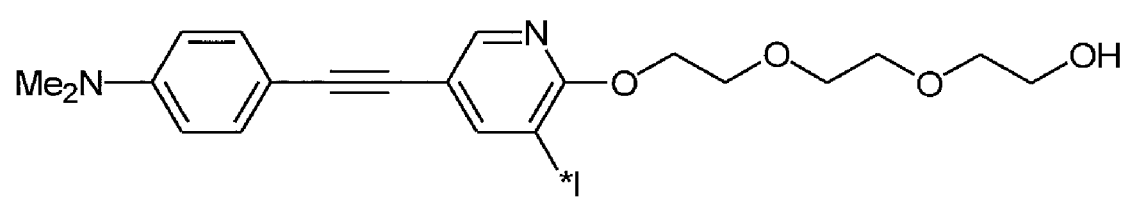
FIG. 3 depicts an ex vivo autoradiograph of a preferred compound of the present invention.
Figure 3:
Figure 4B:
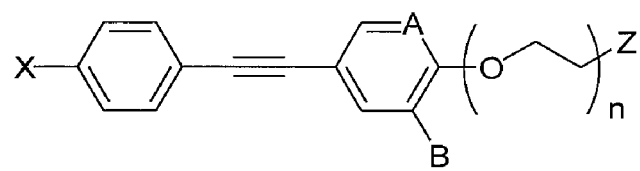
Figure 7:
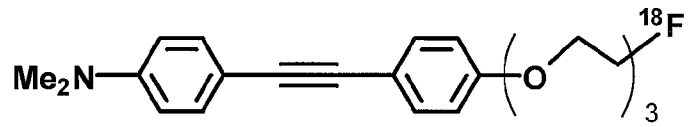
FIGS. 7-10 depict biodistribution in mouse of preferred compounds of the present invention.
Figure 8:
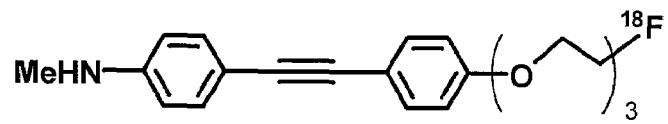
Figure 9:
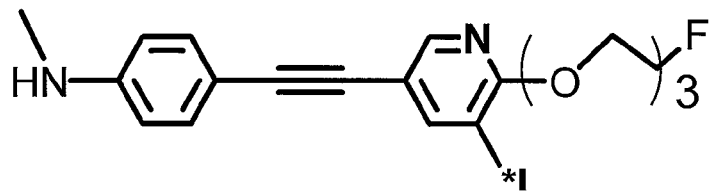
Figure 10:
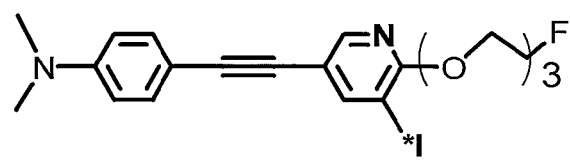

In a first aspect, the present invention is directed to compounds of Formula I:

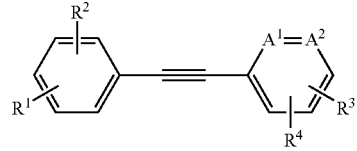

I or a pharmaceutically acceptable salt or prodrug thereof, wherein:
$A^1$ and $A^2$ are independently CH or N;
$R^1$ and $R^2$ are each independently:
  a. NR'R", wherein R' and R" are independently hydrogen, $C_{1-4}$ alkyl, hydroxy($C_{1-4}$)alkyl or halo($C_{1-4}$)alkyl,
  b. hydroxy,
  c. $C_{1-4}$ alkoxy,
  d. hydroxy($C_{1-4}$)alkyl,
  e. halogen,
  f. cyano,
  g. hydrogen,
  h. nitro,
  i. ($C_1$-$C_4$)alkyl,
  j. halo($C_1$-$C_4$)alkyl,
  k. formyl,
  l. —O—CO($C_{1-4}$ alkyl),
  m. —COO($C_{1-4}$ alkyl),
  n. —NHCO($C_{1-4}$ alkyl), or
  o. radiohalogen;
$R^3$ is fragment i, ii or iii, wherein:
  fragment i is:

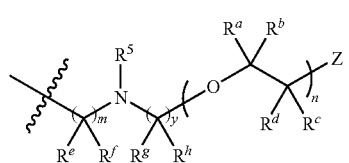

i wherein n is an integer from 1 to 10; m is an integer from 0 to 5; y is an integer from 0 to 5; $R^5$ is hydrogen, $C_{1-4}$ alkyl, or hydroxy($C_{1-4}$)alkyl; $R^a$, $R^b$, $R^c$, $R^d$, $R^e$, $R^f$, $R^g$ and $R^h$ are each independently hydrogen, halogen, hydroxy, $C_{1-4}$ alkoxy, $C_{1-4}$ alkyl, or hydroxy($C_{1-4}$) alkyl; and Z is:
a) X, wherein X is hydrogen, hydroxy, halogen, radiohalogen, $C_{1-4}$ alkoxy, hydroxy($C_{1-4}$)alkyl, halo($C_{1-4}$) alkyl, radiohalo($C_{1-4}$)alkyl or $NR^xR^y$, wherein $R^x$ and $R^y$ are independently hydrogen, $C_{1-4}$ alkyl, hydroxy ($C_{1-4}$)alkyl, radiohalo($C_{1-4}$)alkyl or halo($C_{1-4}$)alkyl;
b) one of the following groups, each of which contains X as a substituent: benzoyloxy, phenyl($C_{1-4}$)alkyl, aryloxy or $C_{6-10}$ aryl;
or
c) Zc, having the following structure:

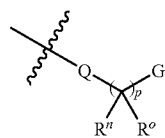

wherein p is an integer from 1 to 4, Q is O or $NR^5$ and G is —C≡C—($R^G$)X or —C≡C—X, wherein $R^G$ is hydrogen or $C_{1-4}$ alkyl, and $R^n$ and $R^o$ are independently hydrogen, hydroxyl or $C_{1-4}$ alkyl;
fragment ii is:

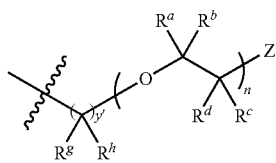

wherein y' is an integer from 0 to 5;
and fragment iii is:

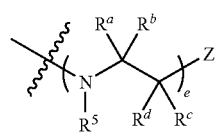

wherein e is 0 or 1;
$R^4$ is hydrogen, halogen, hydroxy, radiohalogen, $C_{1-4}$ alkyl, $C_{1-4}$ alkoxy, hydroxy($C_{1-4}$)alkyl or NR'R";
provided that,
if X is not or does not contain F or $^{18}$F, then $R^4$ is selected from the group consisting of F, $^{18}$F, $^{123}$H, $^{125}$I, $^{131}$I, $^{76}$Br, $^{77}$Br and Br.

In preferred embodiments, $R^1$ is hydroxy, $C_{1-4}$alkoxy, —NHCO($C_{1-4}$ alkyl), —O—CO($C_{1-4}$ alkyl), —COO($C_{1-4}$ alkyl) or NR'R". More preferably, $R^1$ is hydroxy or NR'R", wherein R' and R" are independently hydrogen or $C_{1-4}$alkyl, with $C_{1-4}$alkyl being even more preferred and methyl being particularly preferred.

In other embodiments, $R^2$ is hydroxy, $C_{1-4}$ alkoxy, —NHCO($C_{1-4}$ alkyl), —O—CO($C_{1-4}$ alkyl), —COO($C_{1-4}$ alkyl) or NR'R". Preferably, $R^1$ and $R^2$ are different. Most preferably, $R^2$ is hydrogen.

In still other embodiments, $R^4$ is hydrogen, halogen or radiohalogen. In compounds of the present invention, if X is not or does not contain a halogen or radiohalogen, then $R^4$ is a halogen or radiohalogen. For example, if X is not or does not contain F or $^{18}$F, then $R^4$ is preferably F, $^{18}$F, I, $^{123}$I, $^{125}$I, $^{131}$I, $^{76}$Br, $^{77}$Br or $^{77}$Br.

In preferred embodiments, at least one of $A^1$ and $A^2$ is CH. In those embodiments wherein $A^1$ is N, it is preferred that $A^2$, which is in the meta position relative to the alkyne bridge, is also N.

Each of fragments i, ii, and iii of $R^3$ contains a Z group which, is some preferred embodiments, contains an X moiety. The X moiety is hydrogen, hydroxy, halogen, radiohalogen, $C_{1-4}$ alkoxy, hydroxy($C_{1-4}$)alkyl, halo($C_{1-4}$)alkyl, radiohalo ($C_{1-4}$)alkyl or $NR^xR^y$, wherein $R^x$ and $R^y$ are independently hydrogen, $C_{1-4}$alkyl, hydroxy($C_{1-4}$)alkyl, radiohalo($C_{1-4}$) alkyl or halo($C_{1-4}$)alkyl.

As shown above, fragment i is:

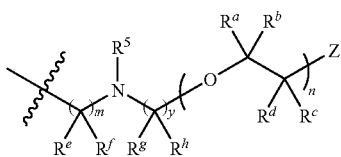

In compounds of the present invention, n is an integer from 1 to 10. Preferably, n is an integer from 1 to 6. More preferably, n is an integer from 2 to 6, and most preferably, n is 3. In all embodiments, m is an integer from 0 to 5. Preferably, m is an integer from 0 to 3. More preferably, m is 0 or 1, and most preferably, m is 0. In compounds of the present invention, y is an integer from 1 to 5. Preferably, y is an integer from 1 to 3. More preferably, y is 1 or 2 and most preferably, y is 2. In preferred compounds of the present invention, $R^5$ is hydrogen, $C_{1-4}$alkyl or hydroxy($C_{1-4}$)alkyl. More preferably, $R^5$ is hydrogen or $C_{1-4}$ alkyl. Most preferably, $R^5$ is hydrogen. In the compounds of the present invention, $R^a$, $R^b$, $R^c$, $R^d$, $R^e$, $R^f$, $R^g$ and $R^h$ are independently hydrogen, halogen, hydroxy, $C_{1-4}$alkoxy, $C_{1-4}$ alkyl or hydroxy($C_{1-4}$)alkyl. Preferably, $R^a$, $R^b$, $R^c$, $R^d$, $R^e$, $R^f$, $R^g$, and $R^h$ are independently hydrogen, hydroxy, hydroxy($C_{1-4}$)alkyl or $C_{1-4}$ alkyl. More preferably, $R^a$, $R^b$, $R^c$, $R^d$, $R^e$, $R^f$, $R^g$ and $R^h$ are independently hydrogen, hydroxy($C_{1-4}$)alkyl or $C_{1-4}$ alkyl, and most preferably, hydroxy($C_{1-4}$)alkyl or hydrogen. In those embodiments where a hydroxy($C_{1-4}$)alkyl is present, it is especially preferred that it be in the $R^c$ or $R^d$ position.

In compounds of the present invention, Z is a) X, wherein X is hydrogen, halogen, radiohalogen, $C_{1-4}$ alkoxy, hydroxy, hydroxy($C_{1-4}$)alkyl, halo($C_{1-4}$)alkyl, radiohalo($C_{1-4}$)alkyl or $NR^xR^y$, wherein $R^x$ and $R^y$ are as described above; b) one of the following groups, each of which contains X as a substitu ent: benzoyloxy, phenyl($C_{1-4}$)alkyl, aryloxy, such as phenoxy, or $C_{6-10}$ aryl; or c) Zc, having the following structure:

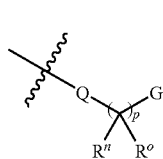

wherein p is an integer from 1 to 4, preferably 2, Q is O or $NR^5$, G is —C=C—($R^G$)X or —C≡C—X, wherein $R^G$ is hydrogen or $C_{1-4}$alkyl, X and $R^5$ are as described above, and $R^n$ and $R^o$ are each independently hydrogen, hydroxy or $C_{1-4}$alkyl.

Structures of Formula I wherein $R^3$ is fragment i include:

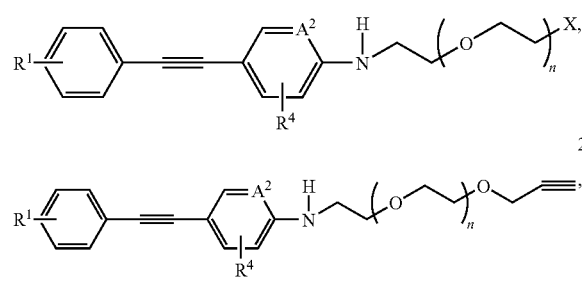

More preferably, compounds of structure 1 are those where n is an integer from 1 to 6; $R^1$ is hydroxy, $C_{1-4}$ alkoxy, —NHCO ($C_{1-4}$ alkyl) or NR'R", wherein R' and R" are independently hydrogen or $C_{1-4}$ alkyl; $R^4$ is hydrogen, $C_{1-4}$ alkyl, $C_{1-4}$ alkoxy, halogen or radiohalogen; and X is hydrogen, halogen, radiohalogen, $C_{1-4}$ alkoxy, hydroxy or $NR^xR^y$, wherein $R^x$ and $R^y$ are as described above; provided that X is or contains F or $^{18}F$, preferably $^{18}F$, and if X is not or does not contain F or $^{18}F$, then $R^4$ is F, $^{18}F$, Br, $^{76}Br$, $^{77}Br$, I, $^{123}I$, $^{125}I$ or $^{131}I$. The most preferred compounds of structure 1 include those of the above proviso and those where n is 3; $R^1$ is hydroxy or —NR'R", wherein R' and R" are independently hydrogen or $C_{1-4}$ alkyl; $R^4$ is hydrogen, halogen or radiohalogen; and X is hydroxy, halogen or radiohalogen.

As shown above, fragment ii is as follows:

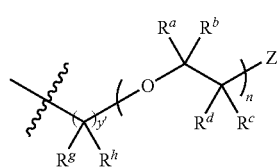

Preferably, y' is an integer from 0 to 5, preferably 0 to 3, and most preferably 0 or 1. In preferred embodiments of Formula I wherein $R^3$ is fragment ii, n is an integer from 1 to 10; y' is an integer from 0 to 3; $R^a$, $R^b$, $R^c$, $R^d$, $R^g$ and $R^h$ are each independently as described above; provided that X is or contains F or $^{18}F$, preferably $^{18}F$, and if X is not or does not contain F or $^{18}F$, then $R^4$ is F, $^{18}F$, Br, $^{76}Br$, $^{77}Br$, I, $^{123}I$ $^{125}I$, or $^{131}I$.

Structures of Formula I wherein $R^3$ is fragment ii include:

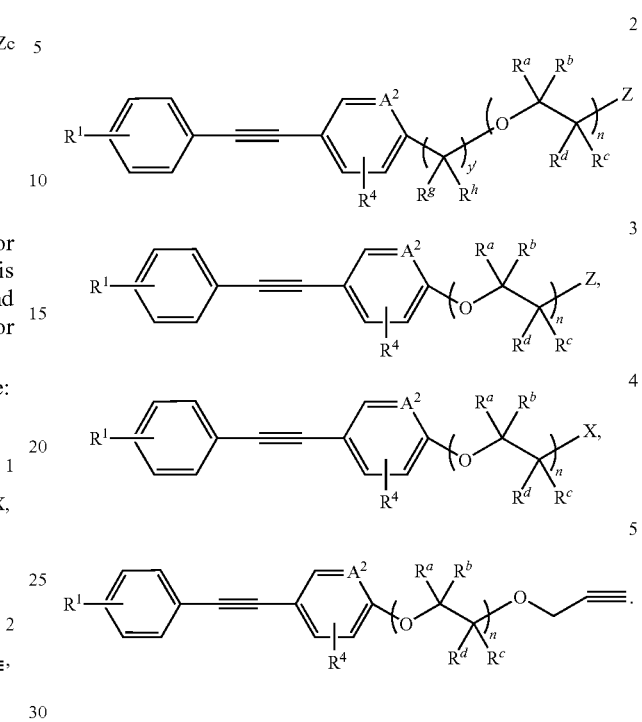

In preferred embodiments were $R^3$ is fragmentii, y' is 1 or 0. Also preferred are those compounds where n is an integer from 2 to 6; $R^1$ is hydroxy, $C_{1-4}$alkoxy, —NHCO($C_{1-4}$ alkyl) or NR'R", wherein R' and R" are independently hydrogen or $C_{1-4}$ alkyl; $R^4$ is hydrogen, $C_{1-4}$ alkyl, $C_{1-4}$ alkoxy, halogen or radiohalogen; and X is hydroxy, halogen, radiohalogen, halo ($C_{1-4}$)alkyl or radiohalo($C_{1-4}$)alkyl, provided that X is or contains F or $^{18}F$, preferably $^{18}F$, and if X is not or does not contain F or $^{18}F$, then $R^4$ is F, $^{18}F$, $^{123}I$, $^{125}I$, $^{131}I$, $^{76}Br$, $^{77}Br$ or Br.

In other preferred embodiments of the present invention, including but not limited to structures of 3, 4 and 5, $A^2$ is N, n is 3 and $R^a$, $R^b$, $R^c$ and $R^d$ are each hydrogen. In other preferred embodiments, $A^2$ is N, n is 1 and $R^a$, $R^b$, and $R^c$ are each hydrogen, $R^d$ is hydroxy($C_{1-4}$)alkyl, and Z is X, wherein X is a halo($C_{1-4}$)alkyl or, more preferably, radiohalo($C_{1-4}$)alkyl.

As shown above, fragment iii is as follows:

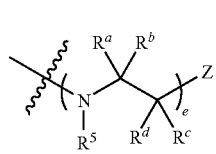

wherein e is 0 or 1. In preferred embodiments wherein $R^3$ is fragment iii, $R^5$, $R^a$, $R^b$, $R^c$ and $R^d$ are each independently as described above and Z is as described above; provided that if X is or contains F or $^{18}F$, preferably $^{18}F$, then $R^4$ is F, $^{18}F$, $^{123}I$, $^{125}I$, $^{76}Br$, $^{77}Br$ or Br.

Structures of Formula I containing fragment iii include:

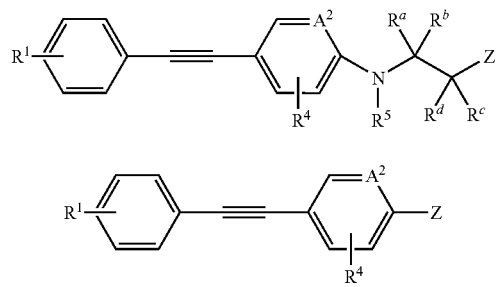

6

7

In preferred embodiments of the present invention that are of structure 6, Z is X, wherein X is hydrogen, halogen, radiohalogen, $C_{1-4}$ alkoxy, hydroxy or $NR^xR^y$, wherein $R^x$ and $R^y$ are as described above; or Zc, having the following structure:

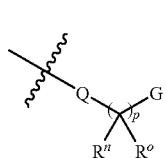

Zc wherein p is an integer from 1 to 4, Q is O or $NR^5$, G is —C≡C—($R^G$)X or —C≡C—X, wherein $R^G$ is hydrogen or $C_{1-4}$ alkyl, $R^n$ and $R^o$ are independently hydrogen, hydroxyl or $C_{1-4}$ alkyl, and X and $R^5$ are as described above.

Other preferred compounds of Formula I have the following structures:

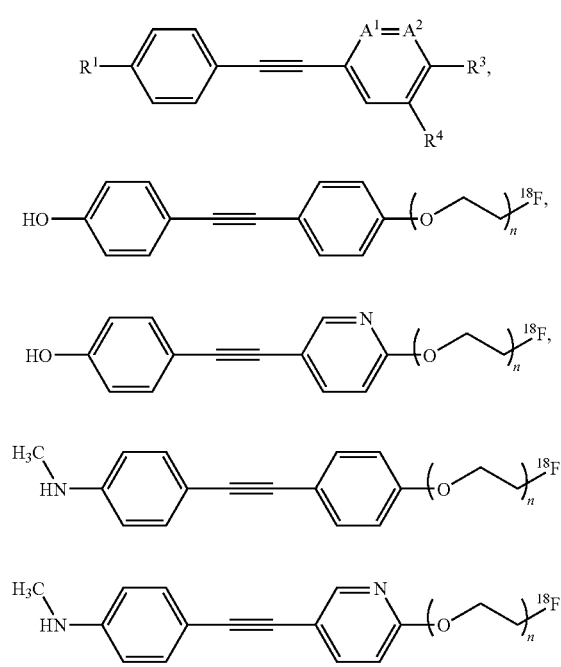

-continued

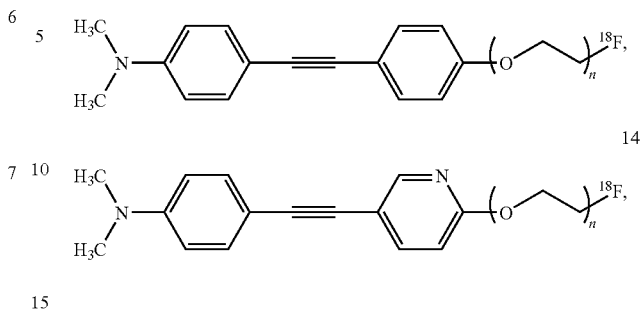

In compounds 9, 10, 11, 12, 13, and 14, n is preferably an integer from 1 to 6. More preferably, n is an integer from 2 to 6. Most preferably, n is 3.

Still other preferred compounds of Formula I include

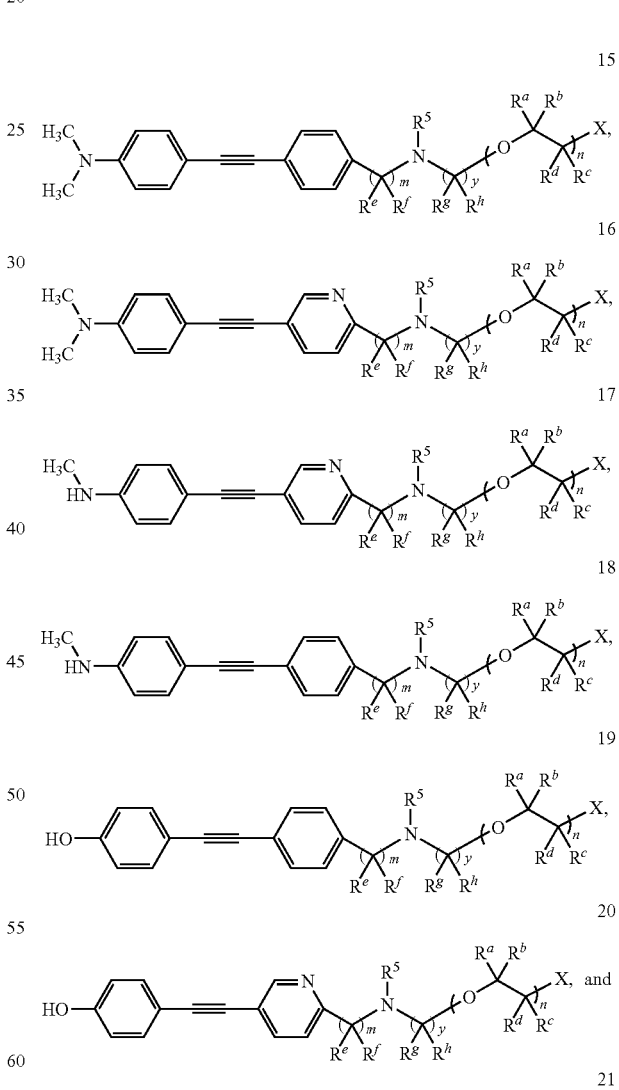

Other embodiments include compounds of structure 22:

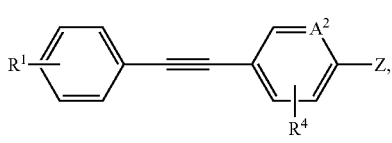
22 wherein $R^1$ is hydroxy or NR'R", wherein R' and R" are independently hydrogen or $C_{1-4}$ alkyl, $A^2$ is CH or N, Z is X, wherein X is hydrogen, hydroxy or $C_{1-4}$ alkoxy, and $R^4$ is I, $^{123}$I, $^{125}$I, $^{131}$I, Br, $^{76}$Br or $^{77}$Br.

Yet other embodiments include:

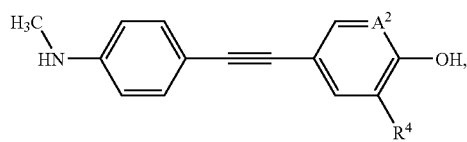
23

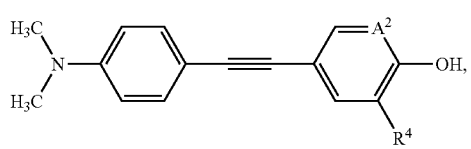
24

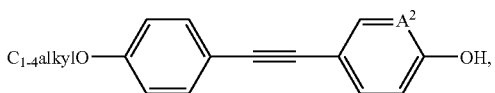
25

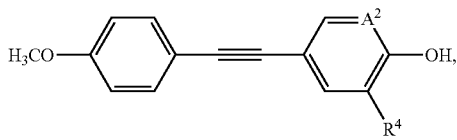
26 wherein $R^4$ is I, $^{123}$I, $^{125}$I, $^{131}$I, Br, $^{76}$Br or $^{77}$Br, more preferably $R^4$ is $^{123}$I, $^{76}$Br or $^{77}$Br.

In other embodiments of the present invention, compounds of Formula I are those of structure 27:

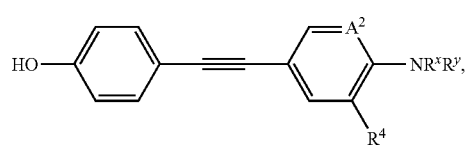
27 wherein $R^x$ and $R^y$ are each independently hydrogen or $C_{1-4}$ alkyl, and $R^4$ is F, $^{18}$F, I, $^{123}$I, $^{125}$I, $^{131}$I, Br, $^{76}$Br or $^{77}$Br, more preferably, $R^4$ is $^{123}$I, $^{76}$Br or $^{77}$Br.

In other embodiments, compounds of Formula I include

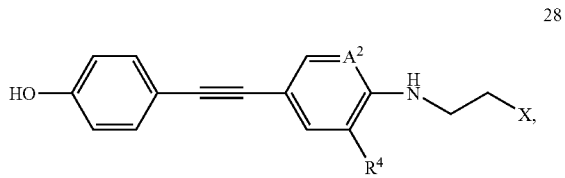
28 wherein $R^4$ is F, $^{18}$F, I, $^{123}$I, $^{125}$I, $^{131}$I, Br, $^{76}$Br or $^{77}$Br, more preferably $R^4$ is $^{123}$I, $^{76}$Br or $^{77}$Br, and X is hydroxy, F or $^{18}$F.

In yet other embodiments, compounds of Formula I include

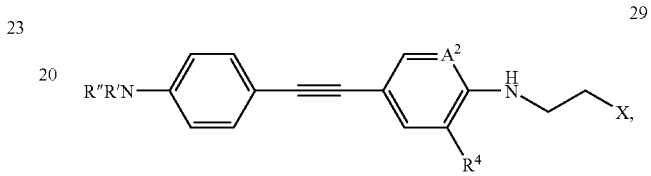
29 wherein R' and R" are each independently hydrogen or $C_{1-4}$ alkyl, $R^4$ is F, $^{18}$F, I, $^{123}$I, $^{125}$I, $^{131}$I, Br, $^{76}$Br or $^{77}$Br, more preferably $R^4$ is $^{123}$I, $^{76}$Br or $^{77}$Br, and X is hydroxy, F or $^{18}$F.

In still other embodiments, compounds of Formula I include

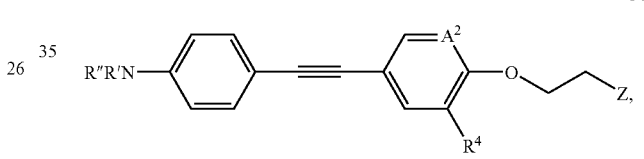
30 wherein R' and R" are each independently hydrogen or $C_{1-4}$ alkyl, $A^2$ is CH or N, $R^4$ is F, $^{18}$F, I, $^{123}$I, $^{125}$I, $^{131}$I, Br, $^{76}$Br or $^{77}$Br, more preferably $R^4$ is $^{123}$I, $^{76}$Br or $^{77}$Br, and Z is X, wherein X is hydroxy, F or $^{18}$F.

In yet other embodiments, compounds of Formula I include

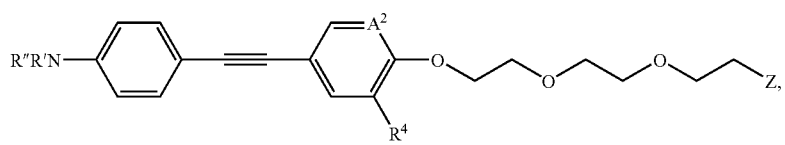
31 wherein R' and R" are each independently hydrogen or $C_{1-4}$ alkyl, and $R^4$ is F, $^{18}$F, I, $^{123}$I, $^{125}$I, $^{131}$I, Br, $^{76}$Br or $^{77}$Br, more preferably $R^4$ is $^{123}$I, $^{76}$Br or $^{77}$Br. More preferably Z is X, wherein X is hydroxy, F, $^{18}$F or Zc, wherein Zc is —OCH$_2$C≡CH.

And in other embodiments, compounds of Formula I include

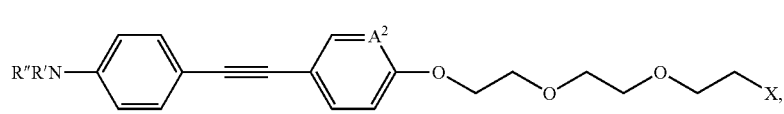
wherein one of R' and R" is $C_{1-4}$ alkyl, preferably methyl, the other of R' and R" is hydrogen or $C_{1-4}$ alkyl, $A^2$ is preferably CH, and X is F or $^{18}F$, preferably $^{18}F$.
Still other embodiments of the present invention include
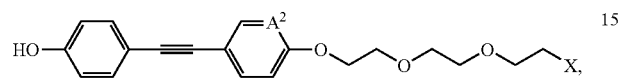
wherein $A^2$ is preferably CH and X is F or $^{18}F$, preferably $^{18}F$.
Most preferably, compounds of Formula I are
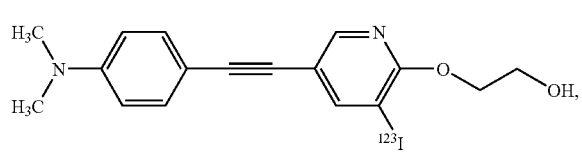
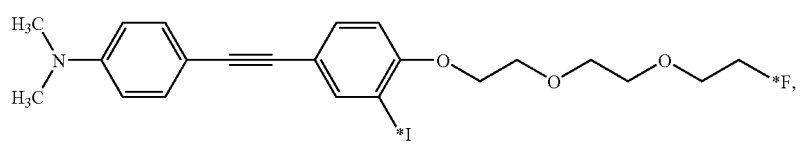
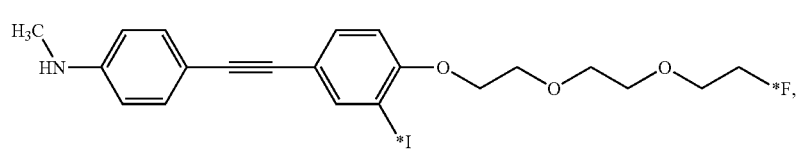
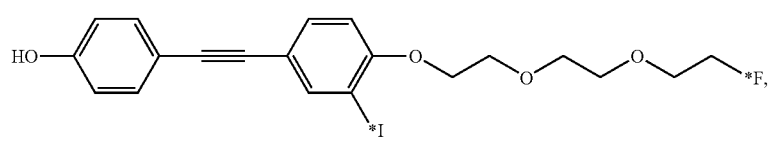
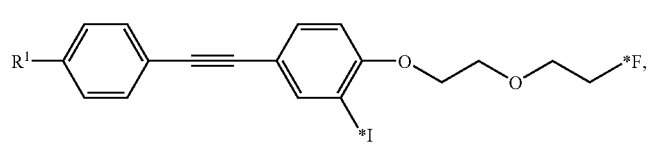
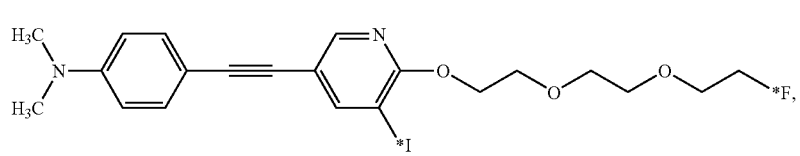

wherein *I and *F are non-radiolabeled or radiolabeled. Preferably, one of *I and *F is radiolabeled, for example, $^{123}$I, or $^{18}$F. Most preferably, *I is $^{123}$I and *F is non-radiolabeled F.

Also preferred are the following compounds:

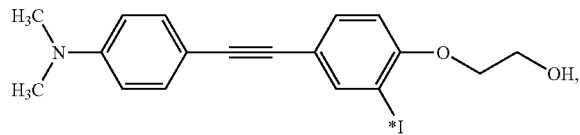

39

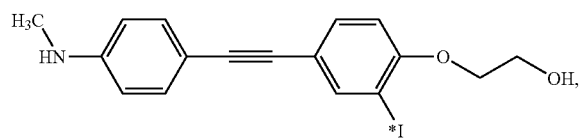

40

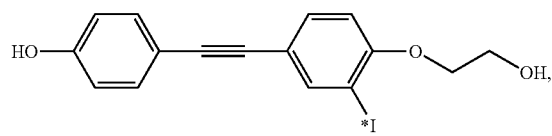

41

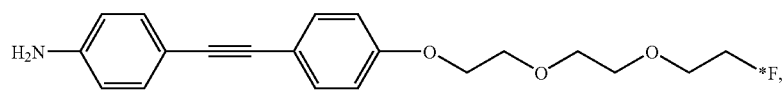

42

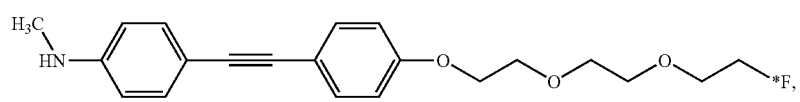

43

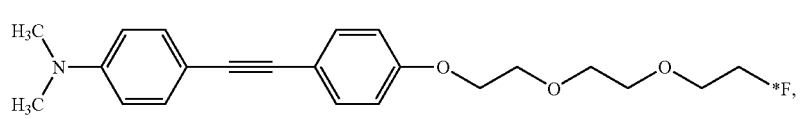

44 wherein *I is radiolabeled or non-radiolabeled. Preferably, *I is radiolabeled. Most preferably, *I is $^{123}$I and wherein *F is radiolabeled or non-radiolabeled. Preferably, *F is $^{18}$F.

Other preferred compounds of Formula I include

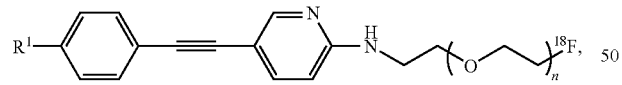

45 wherein R$^1$ is —N(Me)$_2$, —NHMe or hydroxy and n is 1, 2 or 3.

Other compounds of the present invention include hydroxy-branched derivatives such as, for example,

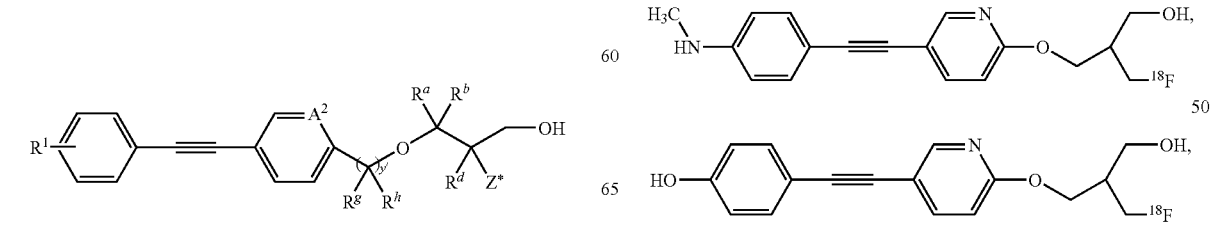

wherein R$^1$ is as described above, A$^2$ is CH or N, y' is an integer from 0 to 5, R$^a$, R$^b$, R$^c$, R$^d$, R$^g$ and R$^h$ are as described above, and Z* is Z or Z', which is described fully below. Especially preferred compounds include those where Z* is a radiohalo(C$_{1-4}$)alkyl, for example, $^{18}$fluoromethyl:

46

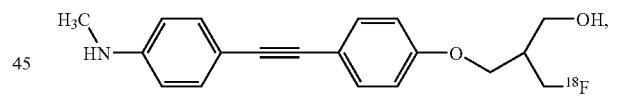

47

48

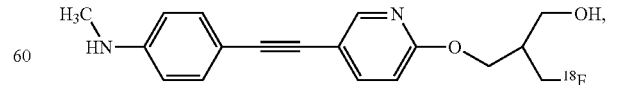

49

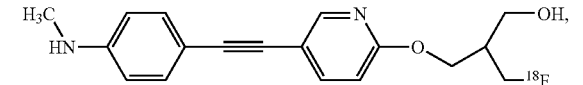

50

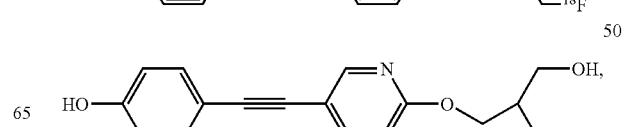

-continued

51: (H3C)2N-C6H4-C≡C-pyridine-O-CH2-CH(OH)-CH2-18F

52: H3C(H)N-C6H4-C≡C-pyridine-O-CH2-CH(OH)-CH2-18F

53: HO-C6H4-C≡C-pyridine-O-CH2-CH(OH)-CH2-18F

54: (H3C)2N-C6H4-C≡C-pyridine-CH2-O-CH2-CH(OH)-CH2-18F

55: H3C(H)N-C6H4-C≡C-C6H4-CH2-O-CH2-CH(OH)-CH2-18F

56: HO-C6H4-C≡C-C6H4-CH2-O-CH2-CH(OH)-CH2-18F, and

57: (H3C)2N-C6H4-C≡C-C6H4-CH2-O-CH2-CH(OH)-CH2-18F.

The present invention is also directed to compounds of Formula II:

$$\text{II}$$

[Structure of Formula II: $R^{21}$–phenyl(–$R^{22}$)–C≡C–ring($A^1$=$A^2$)(–$R^{24}$)–$R^{23}$]

or a pharmaceutically acceptable salt or prodrug thereof, wherein:

$A^1$ and $A^2$ are independently CH or N;
$R^{21}$ and $R^{22}$ are each independently:
a. NR'R", wherein R' and R" are independently hydrogen, $C_{1-4}$ alkyl, hydroxy($C_{1-4}$)alkyl or halo($C_{1-4}$)alkyl;
b. hydroxy,
c. $C_{1-4}$ alkoxy,
d. hydroxy($C_{1-4}$)alkyl,
e. halogen,
f. cyano,
g. hydrogen,
h. nitro,
i. ($C_1$-$C_4$)alkyl,
j. halo($C_1$-$C_4$)alkyl,
k. formyl,
l. —O—CO($C_{1-4}$ alkyl),
m. —COO($C_{1-4}$ alkyl),
n. —NHCO($C_{1-4}$ alkyl), or
o. radiohalogen;

$R^{24}$ is hydrogen, hydroxy, halogen, radiohalogen, $C_{1-4}$ alkyl, $C_{1-4}$ alkoxy, hydroxy($C_{1-4}$)alkyl or NR'R", wherein R' and R" are independently hydrogen, $C_{1-4}$ alkyl, hydroxy($C_{1-4}$)alkyl or halo($C_{1-4}$)alkyl;

$R^{23}$ is fragment i, ii, iii or iv, wherein:

fragment i is:

$$\text{i}$$

[Fragment i structure with $R^5$, $R^a$, $R^b$, $R^c$, $R^d$, $R^e$, $R^f$, $R^g$, $R^h$, N, O, Z', subscripts m, y, n]

wherein n is an integer from 1 to 10; m is an integer from 0 to 5; y is an integer from 1 to 5; $R^5$ is hydrogen, $C_{1-4}$ alkyl, or hydroxy($C_{1-4}$)alkyl; $R^a$, $R^b$, $R^c$, $R^d$, $R^e$, $R^f$, $R^g$ and $R^h$ are each independently hydrogen, halogen, hydroxy, $C_{1-4}$ alkoxy, $C_{1-4}$ alkyl or hydroxy($C_{1-4}$)alkyl; and Z' is:

a) —Ch;
b) one of the following groups, each of which contains a —Ch directly bound to the aromatic ring: benzoyloxy, phenyl($C_{1-4}$)alkyl, aryloxy or $C_{6-10}$ aryl; or
c) Z'c, having the following structure:

$$\text{Z'c}$$

[Z'c structure with Q, G, $R^n$, $R^o$, subscript p]

wherein p is an integer from 1 to 4, Q is O or $NR^5$ and G is —C=C—($R^G$)Ch or —C≡C—Ch, wherein $R^G$ is hydrogen or $C_{1-4}$ alkyl; $R^n$ and $R^o$ are independently hydrogen, hydroxy or $C_{1-4}$ alkyl, $R^5$ is as described herein and Ch is as described below;

fragment ii is:

$$\text{ii}$$

[Fragment ii structure with $R^a$, $R^b$, $R^c$, $R^d$, $R^g$, $R^h$, O, Z', subscripts y, n]

In preferred embodiments, y' is an integer from 0 to 5, preferably 0 to 3, and most preferably 0 or 1;

fragment iii is:

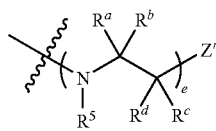

wherein e is 0 or 1, and Z', $R^a$, $R^b$, $R^c$, $R^d$ and $R^5$ are as described above;

and fragment iv is:

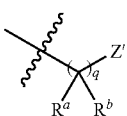

wherein Z', $R^a$ and $R^b$ are as described above, and q is an integer from 1 to 10;

or $R^{23}$ and $R^{24}$ taken together form —Ch.

The moiety —Ch is a chelating ligand capable of complexing with a metal to form a metal chelate. Many ligands are known in the art and are suitable for use as a labeling moiety for compounds of Formula II. Those of skill in the art will understand that such ligands provide a convenient way to label compounds and the invention is not limited to particular ligands, many of which are interchangeable. Preferably, this ligand is a tri- or tetradentate ligand, such as $N_3$, $N_2S$, $NS_2$, $N_4$ and those of the $N_2S_2$ type, such as:

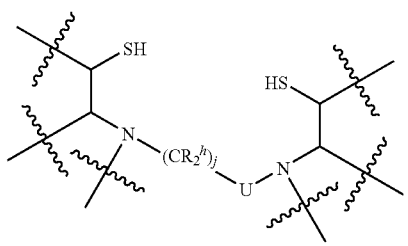

wherein

{ indicates a possible point(s) of attachment of the ligand to the backbone of the amyloid binding structure, j is 0, 1 or 2; and U is two adjacent carbons on the aromatic ring of the backbone or —C($R^{35}R^{36}$)C($R^{37}R^{38}$)—; wherein each $R^h$ and $R^{35}$, $R^{36}$, $R^{37}$ and $R^{38}$ are independently hydrogen, hydroxy, amino, methylamino, dimethylamino, $C_{1-4}$ alkoxy, $C_{1-4}$ alkyl, or hydroxy($C_{1-4}$)alkyl. Preferably, each $R^h$ and $R^{35}$, $R^{36}$, $R^{37}$ and $R^{38}$ are independently hydrogen or $C_{1-4}$ alkyl.

The above ligand can be substituted at other positions, if available, for example:

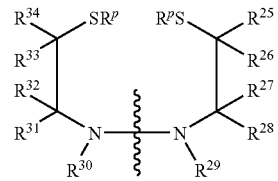

For example, other available positions are represented by $R^{25}$, $R^{26}$, $R^{27}$, $R^{28}$, $R^{29}$, $R^{30}$, $R^{31}R^{32}$, $R^{33}$ and $R^{34}$. In preferred embodiments, $R^{25}$, $R^{26}$, $R^{27}$, $R^{28}$, $R^{29}$, $R^{30}$, $R^{31}$, $R^{32}$, $R^{33}$ and $R^{34}$ are independently hydrogen, hydroxy, amino, methylamino, dimethylamino, $C_{1-4}$ alkoxy, $C_{1-4}$ alkyl, or hydroxy($C_{1-4}$)alkyl. Preferably, $R^{25}$, $R^{26}$, $R^{27}$, $R^{28}$, $R^{29}$, $R^{30}$, $R^{31}$, $R^{32}$, $R^{33}$ and $R^{34}$ are independently hydrogen or $C_{1-4}$ alkyl.

In preferred embodiments, each $R^P$ group is hydrogen or a sulfur protecting group, for example, methoxymethyl, methoxyethoxymethyl, p-methoxybenzyl or benzyl. Sulfur protecting groups are described in detail in Greene, T. W. and Wuts, P. G. M., *Protective Groups in Organic Synthesis*, 2nd Edition, John Wiley and Sons, Inc., New York (1991). Protecting group $R^P$ can be removed by appropriate methods well known in the art of organic synthesis, for example, by treatment with trifluoroacetic acid, mercuric chloride or sodium in liquid ammonia. In the case of Lewis acid labile groups, for example, acetamidomethyl and benzamidomethyl, $R^P$ can be left intact. Labeling of the ligand with technetium in these embodiments will remove the protecting group, rendering the protected diaminedithiol equivalent to the unprotected form.

In preferred embodiments of the present invention, the metal ligand is capable of complexing with a radiometal, for example, $^{99m}Tc$, to form a metal chelate as exemplified by the following structure:

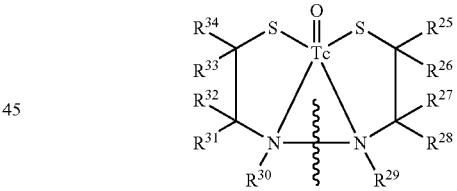

Additionally, other radiometals can be complexed with the ligand, for example, rhenium.

In preferred embodiments, $R^{21}$ is hydroxy, $C_{1-4}$ alkoxy, —NHCO($C_{1-4}$ alkyl) or NR'R", wherein R' and R" are as described above. More preferably, $R^{21}$ is hydroxy or NR'R", wherein R' and R" are independently hydrogen or $C_{1-4}$ alkyl, and in most preferred embodiments, R' and R" are methyl.

In preferred embodiments, $R^{22}$ is hydroxy, $C_{1-4}$ alkoxy, —NHCO($C_{1-4}$ alkyl) or NR'R", wherein R' and R" are as described above. Preferably, $R^{21}$ and $R^{22}$ are different. Most preferably, $R^{22}$ is hydrogen.

Preferably, $R^{24}$ is hydrogen, halogen or $C_{1-4}$ alkyl.

Preferably, one of $A^1$ and $A^2$ is CH and the other of $A^1$ and $A^2$ is CH or N. When $A^1$ is N, it is preferred that $A^2$ is N.

In preferred embodiments, $R^{23}$ is fragment i, ii, iii, or iv. Preferably, each of fragment i, ii, iii, and iv contains a Z' group, wherein each Z' group contains a —Ch moiety. The —Ch moiety is a chelating moiety capable of complexing with a metal to form a chelate. Fragments i, ii, iii and iv are discussed more fully below.

Fragment i is as follows:

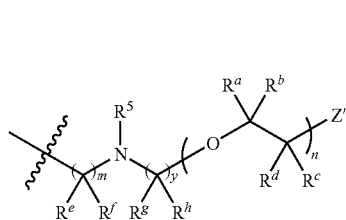

i

In preferred embodiments, n is an integer from 1 to 6. More preferably, n is an integer from 2 to 6, and most preferably, n is 3. In all embodiments, m in an integer from 0 to 5. Preferably, m is an integer from 0 to 3. More preferably, m is 0 or 1 and most preferably, m is 0. Preferably, y is an integer from 0 to 3. More preferably, y is an integer from 0 to 2, and most preferably, y is 2. In preferred embodiments, $R^5$ is hydrogen or $C_{1-4}$ alkyl. Most preferably, $R^5$ is hydrogen. In preferred embodiments, $R^a$, $R^b$, $R^c$, $R^d$, $R^e$, $R^f$, $R^g$ and $R^h$ are each hydrogen, halogen, hydroxy, $C_{1-4}$ alkoxy, $C_{1-4}$ alkyl or hydroxy($C_{1-4}$)alkyl. Preferably, $R^a$, $R^b$, $R^c$, $R^d$, $R^e$, $R^f$, $R^g$ and $R^h$ are each hydrogen, hydroxy or $C_{1-4}$ alkyl. More preferably, $R^a$, $R^b$, $R^c$, $R^d$, $R^e$, $R^f$, $R^g$ and $R^h$ are each hydrogen or $C_{1-4}$ alkyl, and most preferably, $R^a$, $R^b$, $R^c$, $R^d$, $R^e$, $R^f$, $R^g$ and $R^h$ are each hydrogen. Preferably, Z' is:

a) —Ch, wherein —Ch is as described herein;
b) one of the following groups, each of which contains a —Ch directly bound to the aromatic ring: benzoyloxy, phenyl($C_{1-4}$)alkyl, aryloxy or $C_{6-10}$ aryl; or
c) Z'c, having the following structure:

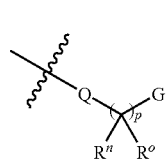

Z'c wherein p is an integer from 1 to 4, preferably 2, Q is O or $NR^5$, G is —C≡C—($R^G$)Ch or —C≡C—Ch, wherein $R^G$ is hydrogen or $C_{1-4}$ alkyl; $R^n$ and $R^o$ are independently hydrogen, hydroxy or $C_{1-4}$ alkyl, and Ch is as described herein.

As shown above, fragment ii is:

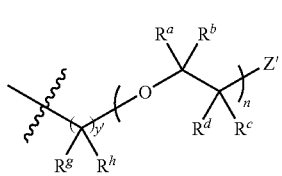

ii wherein n, $R^a$, $R^b$, $R^c$, $R^d$, $R^g$, $R^h$, y' and Z' are as described above. In compounds of Formula II, $R^a$, $R^b$, $R^c$ and $R^d$ are preferably $C_{1-4}$ alkyl or hydrogen. More preferably, $R^a$, $R^b$, $R^c$ and $R^d$ are hydrogen. In preferred embodiments, y' is an integer from 0 to 3. Most preferably, y' is 0 or 1. Preferably, n is an integer from 2 to 6. Most preferably, n is 3. Preferably, Z' is —Ch. In those embodiments where Z' is —Ch, —Ch is preferably a $N_2S_2$ type ligand.

As shown above, fragment iii is:

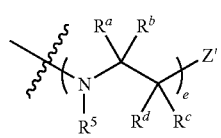

iii wherein e is 0 or 1, and Z', $R^a$, $R^b$, $R^c$, $R^d$ and $R^5$ are as described above. In compounds of Formula II, $R^a$, $R^b$, $R^c$ and $R^d$ are preferably $C_{1-4}$ alkyl or hydrogen and are more preferably hydrogen. Preferably, Z' is —Ch, wherein —Ch is preferably a $N_2S_2$ type ligand.

As shown above, fragment iv is:

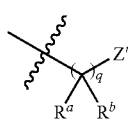

iv wherein Z', $R^a$ and $R^b$ are as described above, and q is an integer from 1 to 10;

or $R^{23}$ and $R^{24}$ taken together form —Ch. In compounds of Formula II, $R^a$ and $R^b$ are preferably $C_{1-4}$ alkyl or hydrogen, and more preferably are hydrogen. In preferred embodiments, q is an integer from 1 to 6. Preferably, q is an integer from 1 to 4. Preferably, Z' is —Ch. In those embodiments where Z' is —Ch, —Ch is preferably a $N_2S_2$ type ligand.

Examples of compounds of Formula II include:

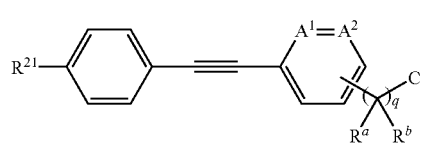

58 wherein $R^{21}$ is hydroxyl, mono- or di($C_{1-4}$)amino; $R^a$ and $R^b$ are independently hydrogen or $C_{1-4}$alkyl; and q is an integer from 1 to 6.

Another example of compounds of Formula II includes

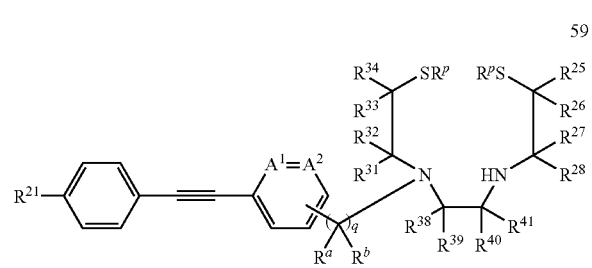

59 wherein $R^{21}$ is hydroxyl, mono- or di($C_{1-4}$)amino; $R^a$ and $R^b$ are independently hydrogen or $C_{1-4}$alkyl; $R^{25}$ through $R^{34}$ are each independently hydrogen or $C_{1-4}$alkyl; and q is an integer from 1 to 6.

Yet another example of compounds of Formula II includes

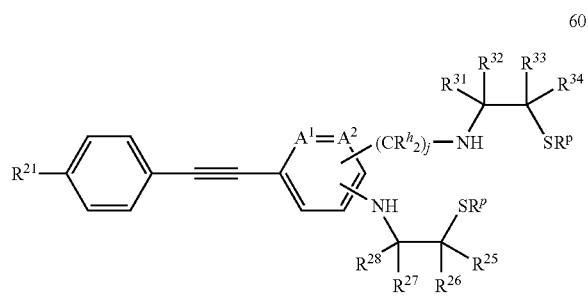

wherein $R^{21}$ is hydroxyl, mono- or di($C_{1-4}$)amino; each $R^h$ is hydrogen or $C_{1-4}$alkyl; j is 1 or 2; and $R^{25}$ through $R^{34}$ are each independently hydrogen or $C_{1-4}$alkyl. The present invention includes those complexes that include a radiometal such as $^{99m}$Tc.

The present invention also includes stereoisomers of compounds of Formulas I and II. Such stereoisomers include optical isomers, e.g. mixtures of enantiomers, as well as individual enantiomers and diastereomers, which may arise as a consequence of structural asymmetry in selected compounds of Formula I or II.

When any variable occurs more than one time in any constituent or in Formula I or II, its definition in each instance is independent of its definition at any other instance. Also, combinations of substituents and/or variables is permissible only if such combinations result in stable compounds.

The compounds of Formulas I and II may also be solvated, especially hydrated. Hydration may occur during manufacturing of the compounds or compositions comprising the compounds, or the hydration may occur over time due to the hygroscopic nature of the compounds. In addition, the compounds of the present invention can exist in unsolvated, as well as solvated forms, with pharmaceutically acceptable solvents such as water, ethanol, and the like. In general, the solvated forms are considered equivalent to the unsolvated forms for the purposes of the present invention.

The present invention is further directed to methods of preparing compounds of the above Formulas I and II. Synthetic routes for preparing compounds of the present invention are described in the following schemes.

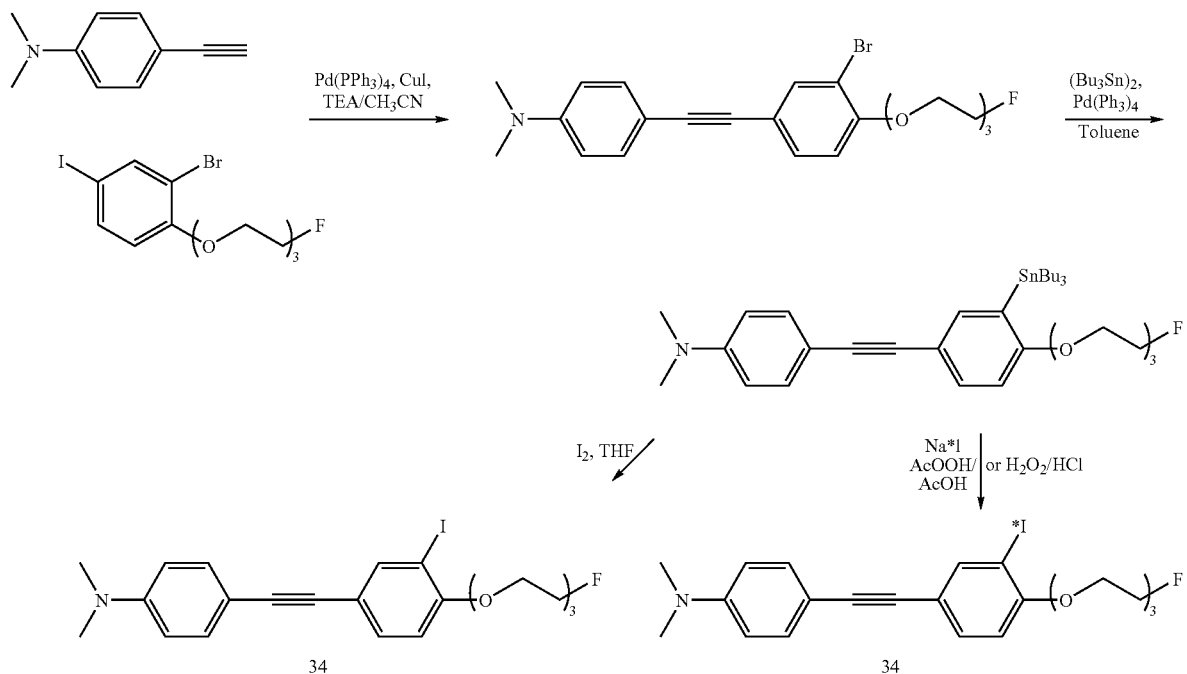

The synthesis strategy in scheme 1 can be used to prepare the monomethylamine compound, 35.

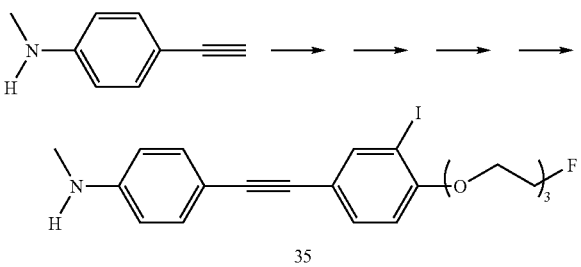

SCHEME 3
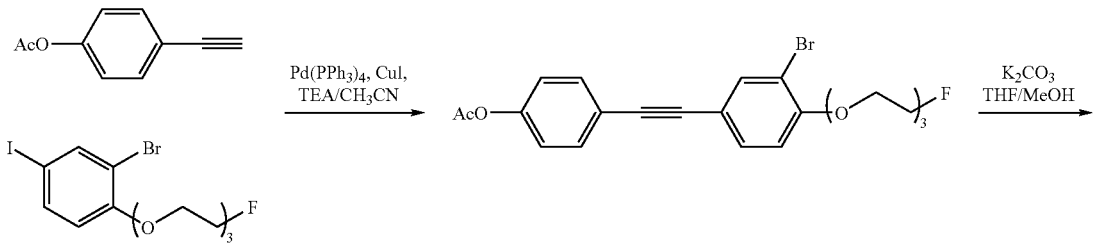
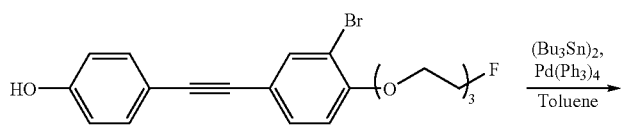
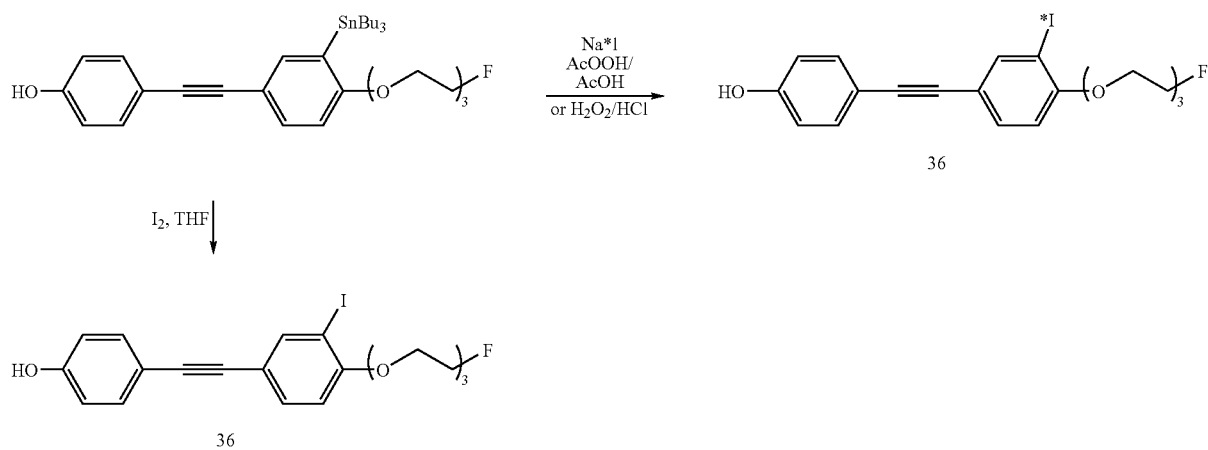
The synthesis strategy in scheme 3 can be used to prepare the derivatives of compounds 37 and 38.
SCHEME 4
SCHEME 5
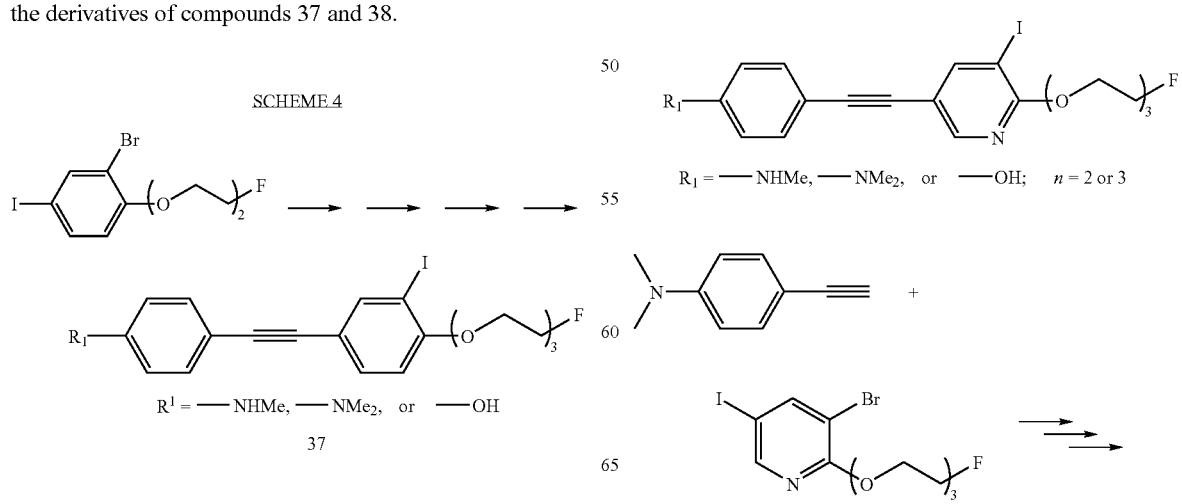
$R_1$ = —NHMe, —NMe$_2$, or —OH;  $n$ = 2 or 3
$R^1$ = —NHMe, —NMe$_2$, or —OH -continued
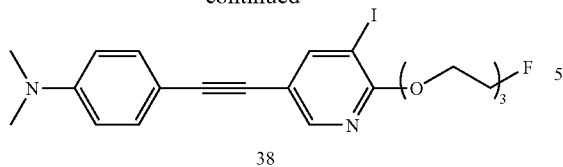
38
-continued
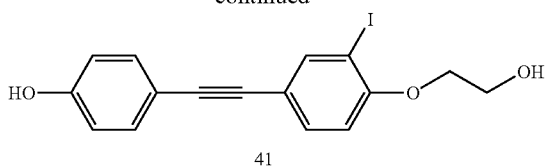
41
SCHEME 6
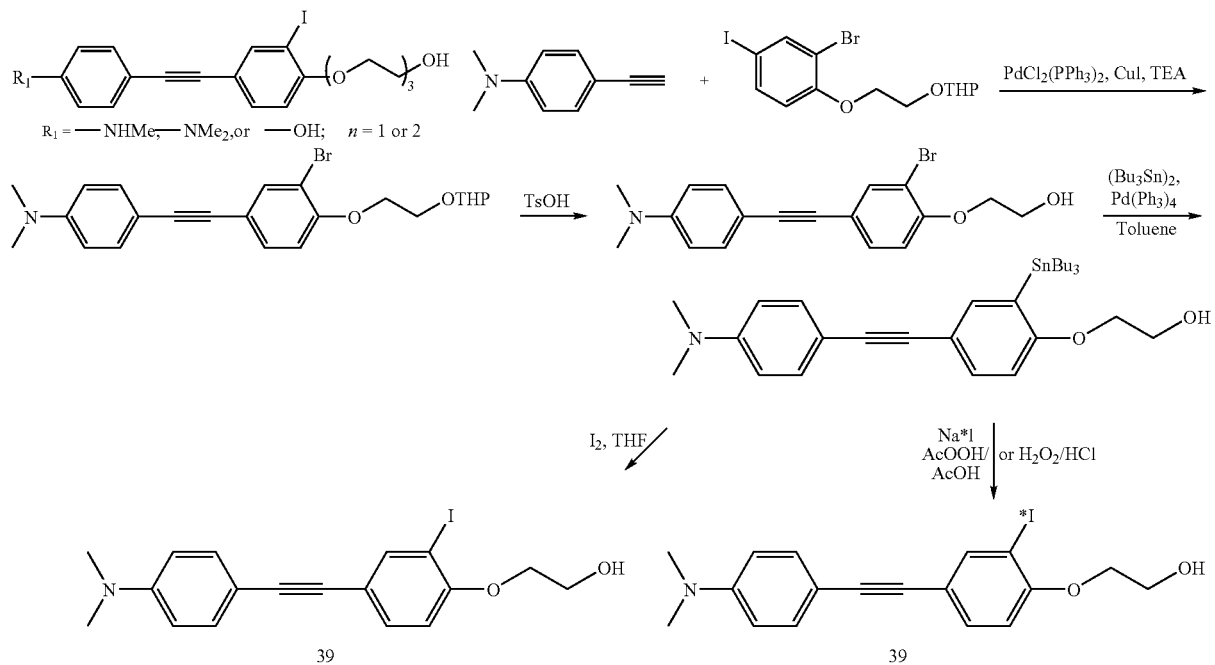
The synthesis strategy in scheme 6 can be used to prepare the monoalkylamine compound, 40, in scheme 7 and the hydroxy compound, 41, in scheme 8.
SCHEME 7
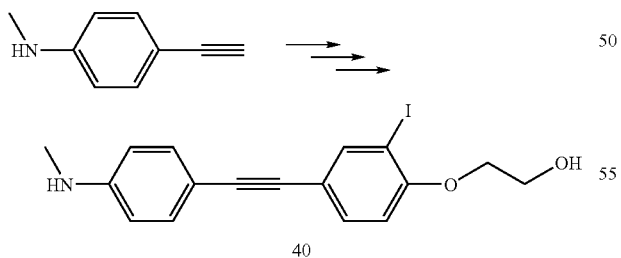
40
SCHEME 8
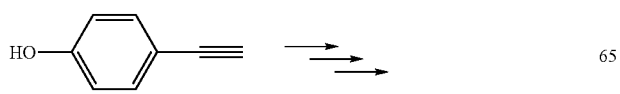
SCHEME 9
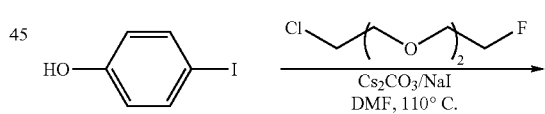
$K_i = 43 \pm 12$ nM
42

SCHEME 10
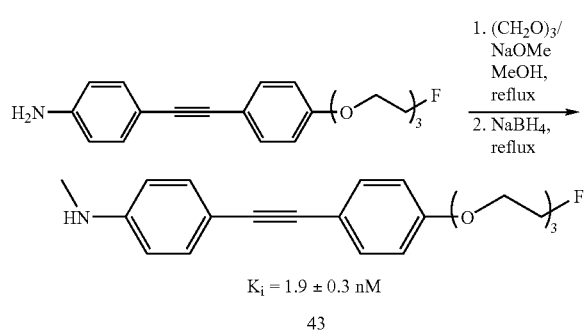
$K_i = 1.9 \pm 0.3$ nM
43
SCHEME 11
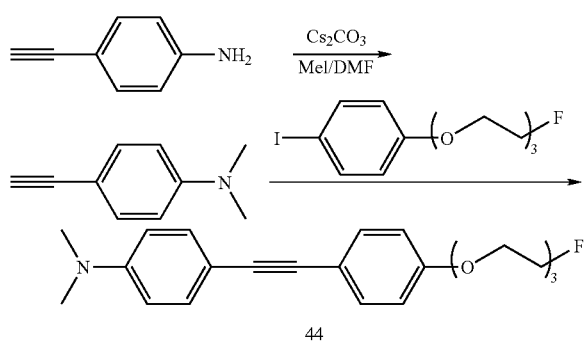
44
SCHEME 12
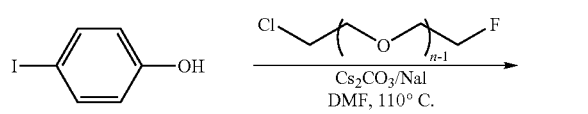
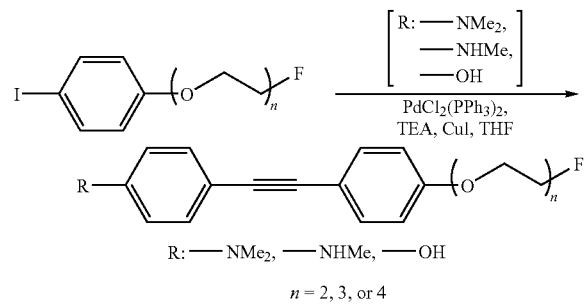
$R$: —$NMe_2$, —$NHMe$, —$OH$
$n = 2, 3,$ or 4
SCHEME 13
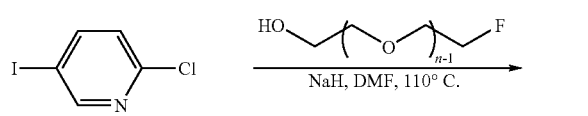
-continued
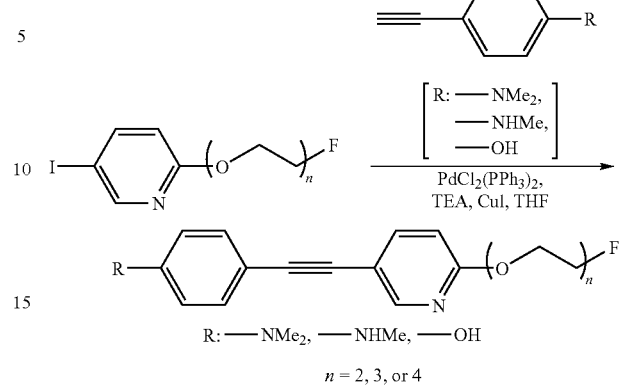
$R$: —$NMe_2$, —$NHMe$, —$OH$
$n = 2, 3,$ or 4
SCHEME 14
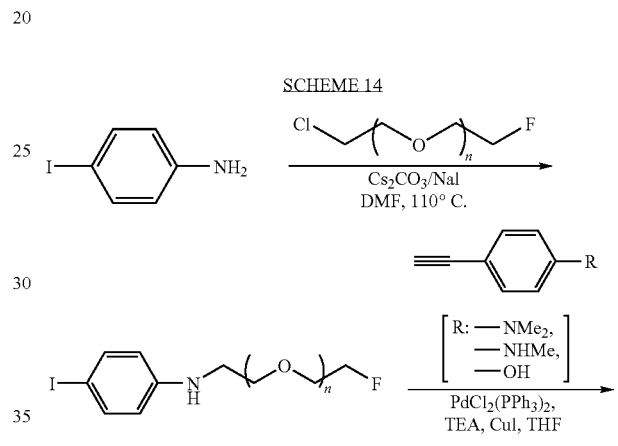
$R$: —$NMe_2$, —$NHMe$, —$OH$
$n = 1, 2,$ or 3
SCHEME 15
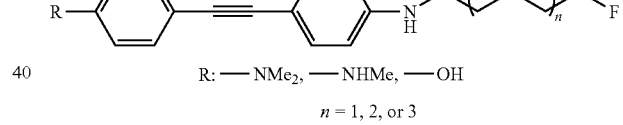
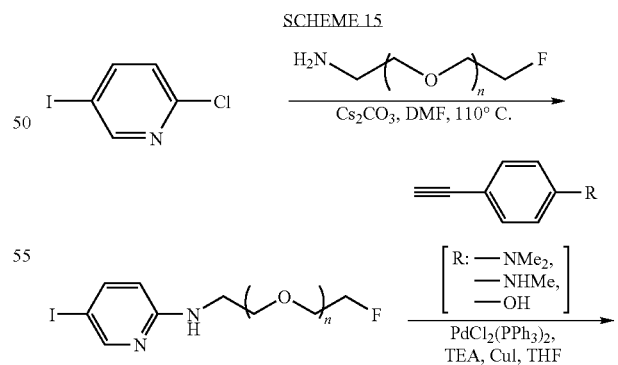
$R$: —$NMe_2$, —$NHMe$, —$OH$
$n = 1, 2,$ or 3

SCHEME 16
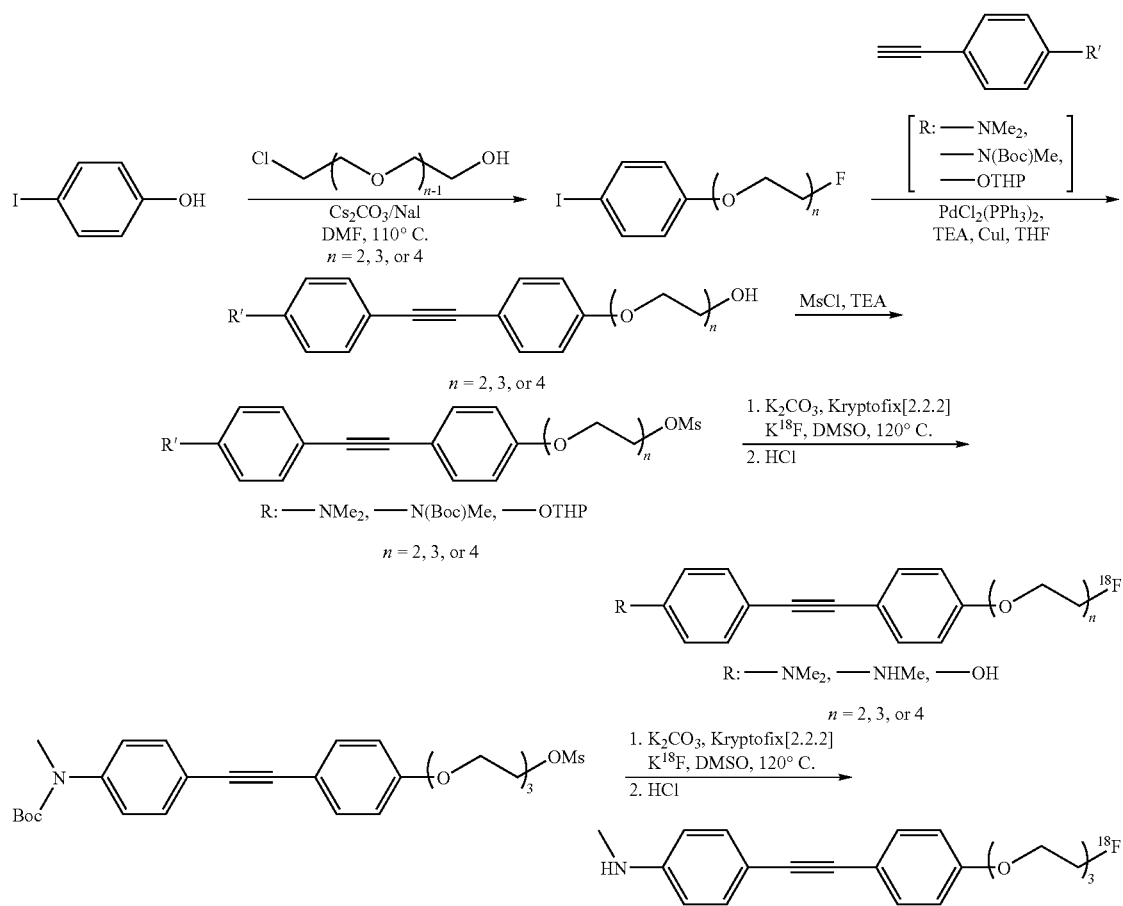
The synthetic strategy of scheme 16 can be used to prepare the pyridine compounds in scheme 17.
SCHEME 17
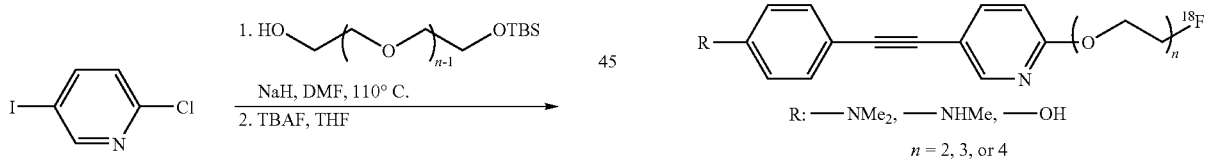
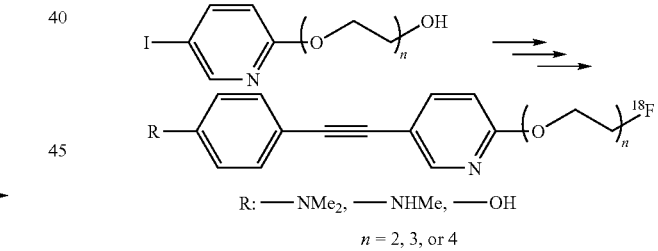
SCHEME 18
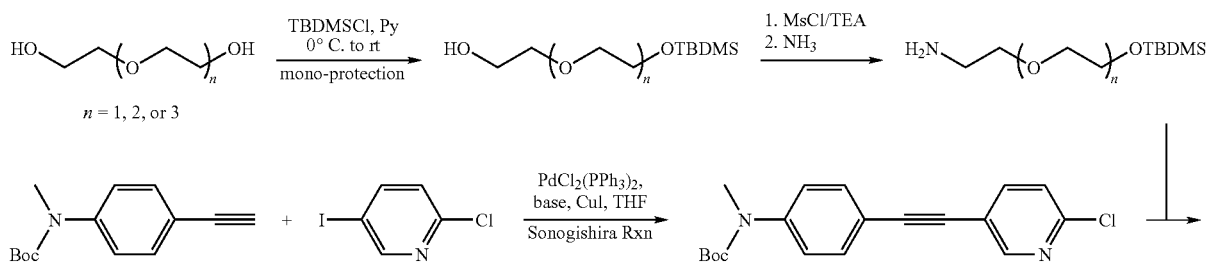

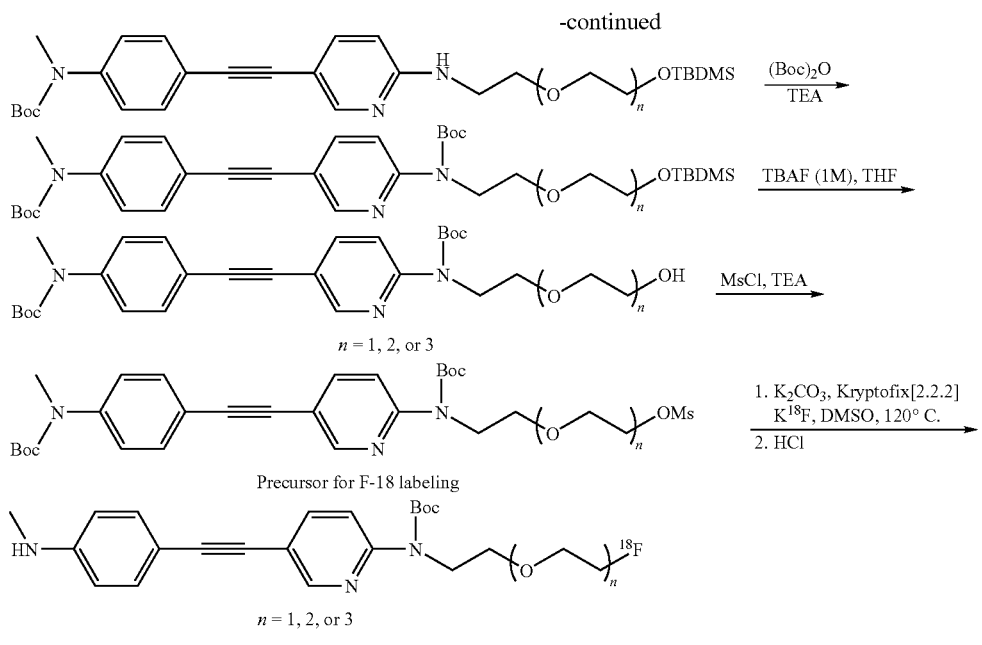

The present invention is also directed at a method of imaging amyloid deposits. When the compounds of this invention are used as imaging agents, they are labeled with suitable radioactive isotopes, for example, radioactive halogens, radioactive metals and other detectable radioactive atoms such as $^{11}C$.

Regarding radiohalogens, $^{125}I$ isotopes are useful for laboratory testing but they will generally not useful for diagnostic purposes because of the relatively long half-life (60 days) and low gamma-emission (30-65 Kev) of $^{125}I$. The isotope $^{123}I$ has a half-life of thirteen hours and gamma energy of 159 KeV, and it is therefore expected that labeling of ligands to be used for diagnostic purposes would be with this isotope or with $^{18}F$ (half-life of 2 hours). Other isotopes which may be used include $^{131}I$, $^{77}Br$, and $^{76}Br$.

In other preferred embodiments, compounds of the present invention also contain a radioactive isotope of carbon as the radiolabel. This refers to a compound that comprises one or more radioactive carbon atoms, preferably $^{11}C$, with a specific activity above that of the background level for that atom. It is well known that naturally occurring elements are present in the form of varying isotopes, some of which are radioactive. The radioactivity of the naturally occurring elements is a result of the natural distribution or abundance of these isotopes, and is commonly referred to as a background level. The carbon labeled compounds of the present invention have a specific activity that is higher than the natural abundance, and therefore above the background level. The carbon-labeled compositions of the present invention can be used for tracing, imaging, radiotherapy, and the like.

A particularly preferred radioactive metal for use in the present invention is Tc-99m. Tc-99m complexes can be prepared as follows: A small amount of non-radiolabeled compound (1-2 mg) is dissolved in 100 µL EtOH and mixed with 200 µL HCl (1 N) and 1 mL Sn-glucoheptonate solution (containing 8-32 µg SnCl$_2$ and 80-320 µg Na-glucoheptonate, pH 6.67) and 50 µL EDTA solution (0.1 N). [$^{99m}Tc$]Pertechnetate (100-200 µL; ranging from 2-20 mCi) saline solution are then added. The reaction is heated for 30 min at 100° C., then cooled to room temperature. The reaction mixture is analyzed on TLC (EtOH:conc. NH$_3$ 9:1) for product formation and purity check. The mixture can be neutralized with phosphate buffer to pH 5.0.

The present invention further relates to a method of preparing a technetium-99m complex according to the present invention by reacting technetium-99m in the form of a pertechnetate in the presence of a reducing agent and optionally a suitable chelator with an appropriate Ch-containing compound.

The reducing agent serves to reduce the Tc-99m pertechnetate which is eluted from a molybdenum-technetium generator in a physiological saline solution. Suitable reducing agents include, for example, dithionite, formamidine sulphinic acid, diaminoethane disulphinate and suitable metallic reducing agents such as Sn(II), Fe(II), Cu(I), Ti(III) and Sb(III). Sn(II) has proven to be particularly suitable.

For the above-mentioned complex-forming reaction, technetium-99m is reacted with an appropriate compound of the invention as a salt or in the form of technetium bound to comparatively weak chelators. In the latter case, the desired technetium-99m complex is formed by ligand exchange. Examples of suitable chelators for the radionuclide are dicarboxylic acids, such as oxalic acid, malonic acid, succinic acid, maleic acid, orthophtalic acid, malic acid, lactic acid, tartaric acid, citric acid, ascorbic acid, salicylic acid or derivatives of these acids; phosphorus compounds such as pyrophosphates; or enolates. Citric acid, tartaric acid, ascorbic acid, glucoheptonic acid or a derivative thereof are particularly suitable chelators for this purpose, because a chelate of technetium-99m with one of these chelators undergoes the desired ligand exchange particularly easily.

The most commonly used procedure for preparing [Tc$^V$O]$^{+3}$N$_2$S$_2$ complexes is based on stannous (II) chloride reduction of [99 mTc]pertechnetate, the common starting material. The labeling procedure normally relies on a Tc-99m ligand exchange reaction between Tc-99m (Sn)-glucoheptonate and the $N_2S_2$ ligand. Preparation of stannous (II) chloride and preserving it in a consistent stannous (II) form is critically important for the success of the labeling reaction. To stabilize the air-sensitive stannous ion it is a common practice in nuclear medicine to use a lyophilized kit, in which the stannous ion is in a lyophilized powder form mixed with an excess amount of glucoheptonate under an inert gas like nitrogen or argon. The preparation of the lyophilized stannous chloride/sodium glucoheptonate kits ensures that the labeling reaction is reproducible and predictable. The $N_2S_2$ ligands are usually air-sensitive and in some instances, subsequent reactions lead to decomposition of the ligands. The most convenient and predictable method to preserve the ligands is to produce lyophilized kits containing 100-500 μg of the ligands under argon or nitrogen.

The radiohalogenated compounds of this invention lend themselves easily to formation from materials which could be provided to users in kits. Kits for forming the imaging agents of the present invention can contain, for example, a vial containing a physiologically suitable solution of an intermediate of Formula I or II in a concentration and at a pH suitable for optimal complexing conditions. The user would add to the vial an appropriate quantity of the radioisotope, e.g., Na $^{123}$I, and an oxidant, such as hydrogen peroxide. The resulting labeled ligand may then be administered intravenously to a patient and receptors in the brain imaged by means of measuring the gamma-ray or photo emissions therefrom.

Since the radiopharmaceutical composition according to the present invention can be prepared easily and simply, the preparation can be carried out readily by the user. Therefore, the present invention also relates to a kit, comprising:

(1) A non-radiolabeled compound of the invention, the compound optionally being in a dry condition; and also optionally having an inert, pharmaceutically acceptable carrier and/or auxiliary substances added thereto; and (2) a reducing agent and optionally, a chelator;

wherein ingredients (1) and (2) may optionally be combined; and further wherein instructions for use with a prescription for carrying out the above-described method by reacting ingredients (1) and (2) with technetium-99m in the form of a pertechnetate solution may be optionally included.

Examples of suitable reducing agents and chelators for the above kit have been listed above. The pertechnetate solution can be obtained by the user from a molybdenum-technetium generator. Such generators are available in a number of institutions that perform radiodiagnostic procedures. As noted above the ingredients (1) and (2) may be combined, provided they are compatible. Such a monocomponent kit, in which the combined ingredients are preferably lyophilized, is excellently suitable to be reacted by the user with the pertechnetate solution in a simple manner.

When desired, the radioactive diagnostic agent may contain any additive such as pH controlling agents (e.g., acids, bases, buffers), stabilizers (e.g., ascorbic acid) or isotonizing agents (e.g., sodium chloride).

Those skilled in the art are familiar with the various ways to detect labeled compounds for imaging purposes. For example, positron emission tomography (PET) or single photon emission computed tomography (SPECT) can be used to detect radiolabeled compounds. The label that is introduced into the compound can depend on the detection method desired. Those skilled in the art are familiar with PET detection of a positron-emitting atom, such as $^{18}$F. The present invention is also directed to specific compounds described herein where the $^{18}$F atom is replaced with a non-radiolabeled fluorine atom. Those skilled in the art are familiar with SPECT detection of a photon-emitting atom, such as $^{123}$I or $^{99m}$Tc. However, the present invention is also directed to specific compounds described herein where the $^{123}$I atom is replaced with a non-radiolabeled iodine atom.

The radioactive diagnostic agent should have sufficient radioactivity and radioactivity concentration which can assure reliable diagnosis. The desired level of radioactivity can be attained by the methods provided herein for preparing compounds of Formula I and II. The imaging of amyloid deposits can also be carried out quantitatively so that the amount of amyloid deposits can be determined.

One of the key prerequisites for an in vivo imaging agent of the brain is the ability to cross the intact blood-brain barrier after a bolus i.v. injection. In the first step of the present method of imaging, a labeled compound of Formula I or II is introduced into a tissue or a patient in a detectable quantity. The compound is typically part of a pharmaceutical composition and is administered to the tissue or the patient by methods well known to those skilled in the art.

For example, the compound can be administered either orally, rectally, parenterally (intravenous, by intramuscularly or subcutaneously), intracisternally, intravaginally, intraperitoneally, intravesically, locally (powders, ointments or drops), or as a buccal or nasal spray.

In preferred embodiments of the invention, the labeled compound is introduced into a patient in a detectable quantity and after sufficient time has passed for the compound to become associated with amyloid deposits, the labeled compound is detected noninvasively. In another embodiment of the invention, a labeled compound of Formula I or II is introduced into a patient, sufficient time is allowed for the compound to become associated with amyloid deposits, and then a sample of tissue from the patient is removed and the labeled compound in the tissue is detected apart from the patient. In a third embodiment of the invention, a tissue sample is removed from a patient and a labeled compound of Formula I is introduced into the tissue sample. After a sufficient amount of time for the compound to become bound to amyloid deposits, the compound is detected.

The administration of the labeled compound to a patient can be by a general or local administration route. For example, the labeled compound may be administered to the patient such that it is delivered throughout the body. Alternatively, the labeled compound can be administered to a specific organ or tissue of interest. For example, it is desirable to locate and quantitate amyloid deposits in the brain in order to diagnose or track the progress of Alzheimer's disease in a patient.

Another aspect of the invention is a method of inhibiting amyloid plaque aggregation. The present invention also provides a method of inhibiting the aggregation of amyloid proteins to form amyloid deposits, by administering to a patient an amyloid inhibiting amount of a compound of Formula I or II.

The compounds of the present invention can be administered to a patient at dosage levels in the range of about 0.1 to about 1,000 mg per day. For a normal human adult having a body weight of about 70 kg, a dosage in the range of about 0.01 to about 100 mg per kilogram of body weight per day is sufficient. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

Those skilled in the art are readily able to determine an amyloid inhibiting amount by simply administering a compound of Formula I or II to a patient in increasing amounts until the growth of amyloid deposits is decreased or stopped. The rate of growth can be assessed using imaging as described above or by taking a tissue sample from a patient and observing the amyloid deposits therein.

The compounds of the present invention may be used in combination with one or more other drugs in the treatment, prevention, control, amelioration, or reduction of risk of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with: anti-Alzheimer's agents, for example beta-secretase inhibitors or gamma-secretase inhibitors; HMG-CoA reductase inhibitors; NSAIDs including ibuprofen; vitamin E; anti-amyloid antibodies, including humanized monoclonal antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil and tacrine; growth hormone secretagogues such as ibutamoren, ibutamoren mesylate, and capromorelin; histamine $H_3$ antagonists; AMPA agonists; PDE IV inhibitors; GABAa inverse agonists; neuronal nicotinic agonists; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The term "pharmaceutically acceptable salt" as used herein refers to those carboxylate salts or acid addition salts of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. Also included are those salts derived from non-toxic organic acids such as aliphatic mono and dicarboxylic acids, for example acetic acid, phenyl-substituted alkanoic acids, hydroxy alkanoic and alkanedioic acids, aromatic acids, and aliphatic and aromatic sulfonic acids. These salts can be prepared in situ during the final isolation and purification of the compounds or by separately reacting the purified compound in its free base form with a suitable organic or inorganic acid and isolating the salt thus formed. Further representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, propionate, pivalate, cyclamate, isethionate, and the like. These may include cations based on the alkali and alkaline earth metals, such as sodium, lithium, potassium, calcium, magnesium, and the like, as well as, nontoxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, Berge S. M., et al., *Pharmaceutical Salts, J. Pharm. Sci.* 66:1-19 (1977) which is incorporated herein by reference.)

The term "alkyl" as employed herein by itself or as part of another group refers to both straight and branched chain radicals of up to 4 carbons, preferably 1 or 2 carbons, more preferably 1 carbon (methyl).

The term "alkoxy" is used herein to mean a straight or branched chain alkyl radical, as defined above, unless the chain length is limited thereto, bonded to an oxygen atom, including, but not limited to, methoxy, ethoxy, n-propoxy, isopropoxy, and the like. Preferably the alkoxy chain is 1 to 4 carbon atoms in length, more preferably 1 or 2 carbon atoms in length.

The term "monoalkylamine" as employed herein by itself or as part of another group refers to an amino group which is substituted with one alkyl group as defined above. The term "dialkylamine" refers to an amino group which is substituted with two alkyl groups, which are defined above.

The term "halo" or "halogen" employed herein by itself or as part of another group refers to chlorine, bromine, fluorine or iodine, unless defined otherwise in specific uses in the text and/or claims.

The term "radiohalogen" employed herein by itself or as part of another group refers to $^{18}F$, $^{19}F$, $^{123}I$, $^{125}I$, $^{131}I$, $^{76}Br$ and $^{77}Br$.

The term "halo($C_{1-4}$)alkyl" as employed herein refers to any of the above alkyl groups substituted by one or more chlorine, bromine, fluorine or iodine with fluorine being preferred. Useful groups are chloromethyl, iodomethyl, trifluoromethyl, 2,2,2-trifluoroethyl, and 2-chloroethyl. Most preferably, the alkyl is substituted with a single halo, such as fluorine, at the distal end of the alkyl. The term "radiohalo ($C_{1-4}$)alkyl" refers to a halo($C_{1-4}$)alkyl group as defined above that contains a halogen radioisotope. One example of this type of group is $^{18}F$—($C_{1-4}$)alkyl-.

The term "hydroxyalkyl" as employed herein by itself or as part of another group refers to linear or branched alkyl groups containing an —OH substituent.

The term "aryl" as employed herein by itself or as part of another group refers to monocyclic or bicyclic aromatic groups containing from 5 to 14 atoms in the ring portion, preferably 6-10 carbons in the ring portion, such as phenyl, naphthyl or tetrahydronaphthyl. As employed herein, each aryl contains X or —Ch as a substituent. Preferable values under the scope of $C_{6-10}$ aryl include the following moieties, each of which contains X or —Ch as a substituent: phenyl, naphthyl and tetrahydronaphthyl. The aryl group can also contain a heteroatom, such as N, S or O to form a "heteroaryl." Preferable values of under the scope of heteroaryl include: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups.

The term "aryloxy" as employed herein refers to an "aryl" group bonded to an oxygen atom, and include benzyloxy and phenoxy and the like. Benzoyloxy refers to an ester.

The term "tissue" means a part of a patient's body. Examples of tissues include the brain, heart, liver, blood vessels, and arteries. A detectable quantity is a quantity of labeled compound necessary to be detected by the detection method chosen. The amount of a labeled compound to be introduced into a patient in order to provide for detection can readily be determined by those skilled in the art. For example, increasing amounts of the labeled compound can be given to a patient until the compound is detected by the detection method of choice. A label is introduced into the compounds to provide for detection of the compounds.

The term "patient" means humans and other animals. Those skilled in the art are also familiar with determining the amount of time sufficient for a compound to become associated with amyloid deposits. The amount of time necessary can easily be determined by introducing a detectable amount of a labeled compound of Formula I or II into a patient and then detecting the labeled compound at various times after administration.

The term "associated" means a chemical interaction between the labeled compound and the amyloid deposit. Examples of associations include covalent bonds, ionic bonds, hydrophilic-hydrophilic interactions, hydrophobic-hydrophobic interactions, and complexes.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

Aβ Aggregate Binding Affinities

Alkyne derivatives which can be synthesized according to a method disclosed herein display excellent binding affinities to Aβ plaques. Examples of core structures containing iodine or bromine atom and their respective binding affinities are shown in FIG. 1. The competitive binding assay was performed using [$^{125}$I]IMPY as the ligand in pooled brain tissue homogenates of confirmed AD patients. Values are the mean ±SEM of three independent experiments, each in duplicate.

EXAMPLE 2

A compound of the present invention is testing in an established in-vitro immunoblot assay for its ability to inhibit the formation of Aβ oligomers and fibrils. (Yang F, Lim G P, Begum A N, et al. *Curcumin inhibits formation of amyloid β oligomers and fibrils, binds plaques, and reduces amyloid in-vivo. J. Biol. Chem.* 280:5892-5901, 2005). Curcumin, a natural molecule serves as positive control. Acetylene compounds of this invention are able to inhibit the aggregation Aβ in a manner similar to Curcumin at concentrations of 1-100 μM.

It will be understood to those of ordinary skill in the art that the same can be performed within a wide and equivalent range of conditions, formulations, and other parameters without affecting the scope of the invention or any embodiment thereof. All patents, patent applications, and publications cited herein are fully incorporated by reference herein in their entirety.

What is claimed:

1. A compound of Formula I,

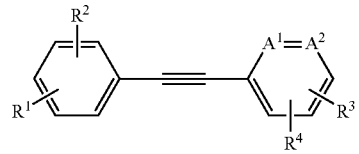

or a pharmaceutically acceptable salt thereof, wherein:

$A^1$ is CH $A^2$ is CH or N;

$R^1$ and $R^2$ are each independently:

hydrogen, —NHC$_{1-4}$alkyl, —N(C$_{1-4}$alkyl)$_2$, —NH$_2$, C$_{1-4}$alkoxy or —OH;

$R^3$ fragment i, ii or iii, wherein:

fragment i is:

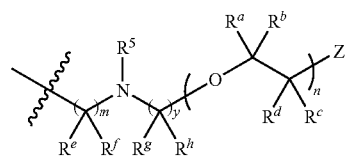

wherein n is an integer from 1 to 10; m is an integer from 0 to 5; y is an integer from 0 to 5;

$R^5$ is hydrogen, C$_{1-4}$ alkyl, or hydroxy(C$_{1-4}$)alkyl; $R^a$, $R^b$, $R^c$, $R^d$, $R^e$, $R^f$, $R^g$ and $R^h$ are each independently hydrogen, halogen, hydroxy, C$_{1-4}$ alkoxy, C$_{1-4}$ alkyl, or hydroxy(C$_{1-4}$)alkyl; and Z is:

a) X, wherein X is hydrogen, hydroxy, halogen, radiohalogen, C$_{1-4}$ alkoxy, hydroxy(C$_{1-4}$)alkyl, halo(C$_{1-4}$)alkyl, radiohalo(C$_{1-4}$)alkyl or NR$^x$R$^y$, wherein R$^x$ and R$^y$ are independently hydrogen, C$_{1-4}$ alkyl, hydroxy(C$_{1-4}$)alkyl, radiohalo(C$_{1-4}$)alkyl or halo(C$_{1-4}$)alkyl;

b) one of the following groups, each of which contains X as a substituent:

benzoyloxy, phenyl(C$_{1-4}$)alkyl, aryloxy or C$_{6-10}$ aryl;

or c) Zc, having the following structure:

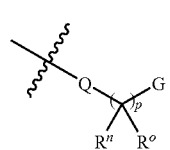

wherein p is an integer from 1 to 4, Q is O or NR$^5$ and G is —C═C—(R$^G$)X or —C≡C—X, wherein R$^G$ is hydrogen or C$_{1-4}$ alkyl, and R$^n$ and R$^o$ are independently hydrogen, hydroxyl or C$_{1-4}$alkyl;

fragment ii is:

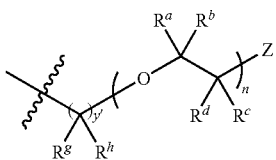

wherein y' is an integer from 0 to 5;
and fragment iii is:

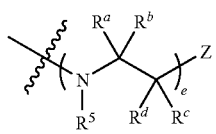

wherein e is 0 or 1;
R$^4$ is hydrogen, halogen, or radiohalogen;
provided that,
if X is not or does not contain F or $^{18}$F, then R$^4$ is F, $^{18}$F $^{123}$I, $^{125}$I, $^{131}$I, $^{76}$Br, or $^{77}$Br or Br.

2. The compound of claim 1, wherein R$^2$ is hydrogen.
3. The compound of claim 1, wherein A$^2$ is N.
4. The compound of claim 1, wherein A$^2$ is CH.
5. The compound of claim 1, wherein R$^3$ is

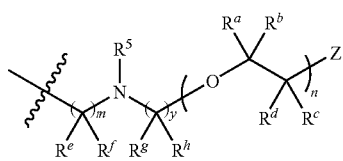

wherein
y is an integer from 1 to 5.

6. The compound of claim 5, wherein:
n is an integer from 1 to 6;
m is an integer from 0 to 3; and
y is an integer from 1 to 3.

7. The compound of claim 6, wherein:
n is an integer from 2 to 6;
m is 0; and
y is 2.

8. The compound of claim 5, wherein R$^a$, R$^b$, R$^c$, R$^d$, R$^e$, R$^f$, R$^g$ and R$^h$ are each hydrogen.

9. The compound of claim 5 that is:

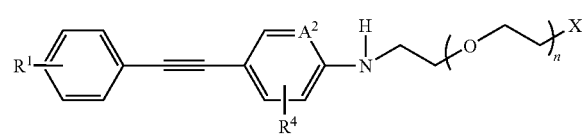

wherein
n is an integer from 1 to 6;
and
X is hydrogen, halogen, radiohalogen, C$_{1-4}$alkoxy, hydroxy or NR$^x$R$^y$; provided that,
X is or contains $^{18}$F or R$^4$ is $^{123}$I, $^{125}$I, or $^{131}$I.

10. The compound of claim 9, wherein:
n is 3;
R$^1$ is hydroxy, —NHC$_{1-4}$alkyl, —N(C$_{1-4}$alkyl)$_2$, or —NH$_2$;
and
X is hydroxy, halogen or radiohalogen.

11. The compound of claim 1, wherein R$^3$ is

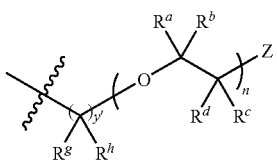

provided that,
X is $^{18}$F or R$^4$ is $^{123}$I, $^{125}$I or $^{131}$I.

12. The compound of claim 1 that is:

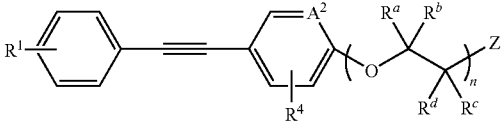

wherein
n is an integer from 2 to 6;
and
X is hydroxy, halogen or radiohalogen;
provided that,
X is $^{18}$F or R$^4$ is $^{123}$I, $^{125}$I or $^{131}$I.

13. The compound of claim 12, wherein A$^2$ is N.
14. The compound of claim 12, wherein R$^a$, R$^b$, R$^c$ and R$^d$ are hydrogen.
15. The compound of claim 12, wherein n is 3.
16. The compound of claim 1, wherein R$^3$ is

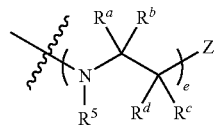

provided that,
X is or contains $^{18}$F or R$^4$ is $^{123}$I, $^{125}$I or $^{131}$I.

17. The compound of claim 16, wherein e is 1.
18. The compound of 17, wherein:
Z is:
X, wherein X is hydrogen, halogen, radiohalogen, C$_{1-4}$ alkoxy, hydroxy or NR'R''; or
Zc, having the following structure:

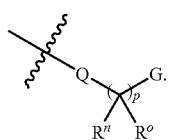

19. A pharmaceutical composition comprising a compound of claim 1 and a pharmaceutically acceptable excipient.

20. A diagnostic composition for imaging amyloid deposits, comprising a radiolabeled compound of claim 1 and a pharmaceutically acceptable excipient.

21. A method of imaging amyloid deposits in a patient, comprising:
a. introducing into the patient a detectable quantity of a diagnostic composition of claim 20;
b. allowing sufficient time for the labeled compound to be associated with amyloid deposits; and c. detecting the labeled compound associated with one or more amyloid deposits.
22. The compound of claim 1 that is
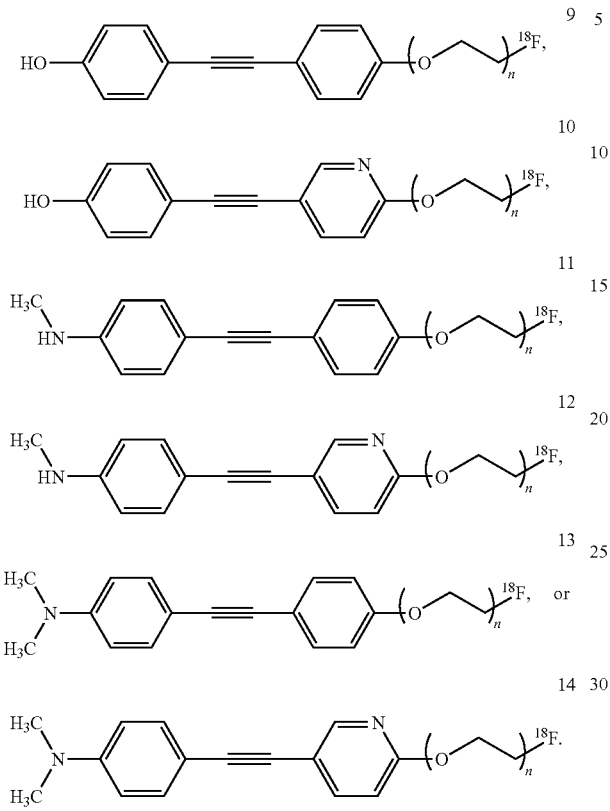
23. The compound of claim 1 that is
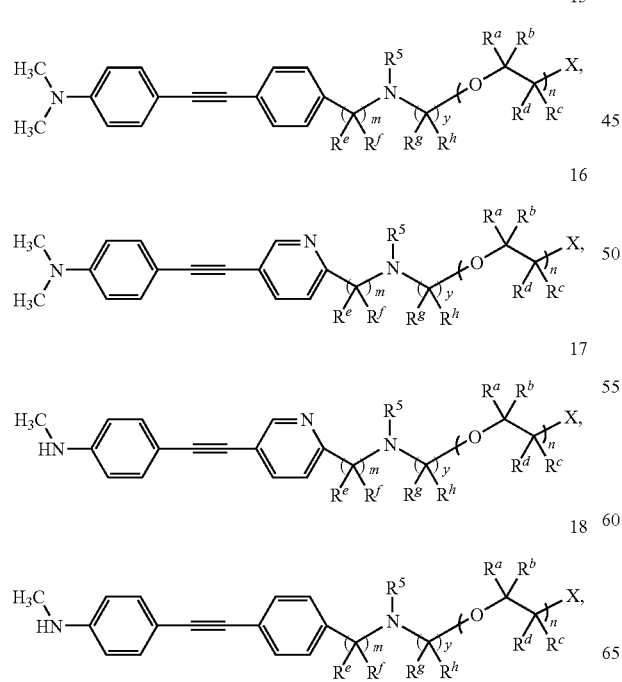
-continued
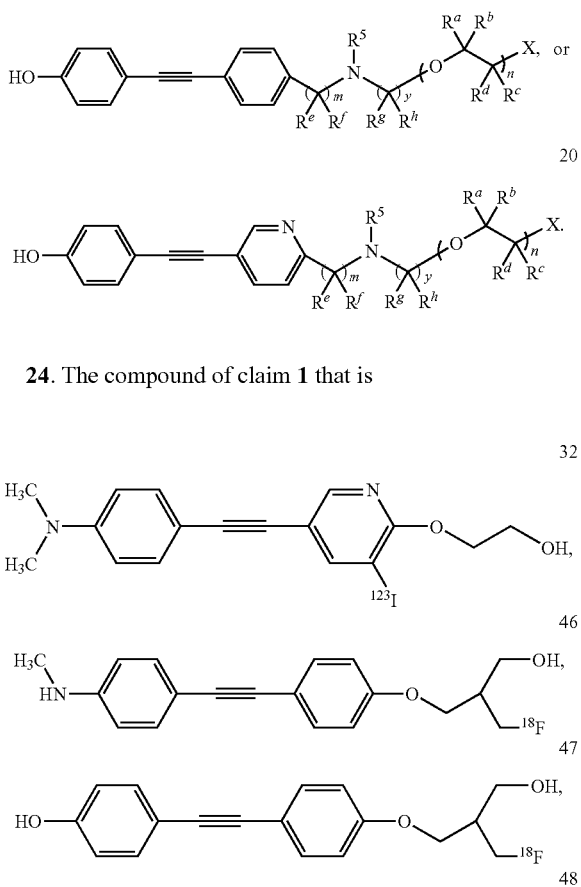
24. The compound of claim 1 that is

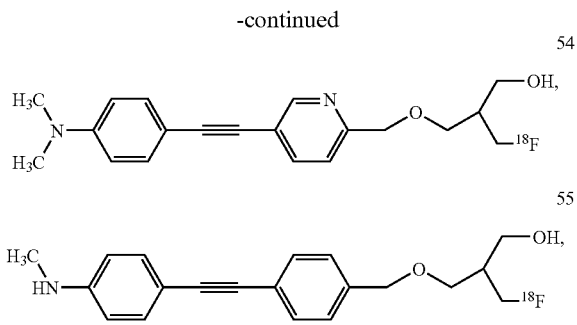
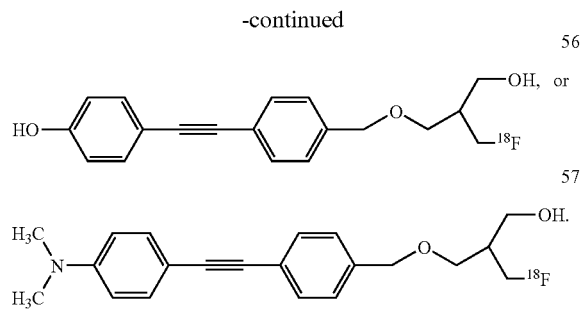
* * * * *